United States Patent
Bodurka et al.

(10) Patent No.: US 11,727,740 B1
(45) Date of Patent: Aug. 15, 2023

(54) ENTRY ACCESS SYSTEM AND METHOD WITH QUESTIONNAIRE SCREENING

(71) Applicant: Masonite Corporation, Tampa, FL (US)

(72) Inventors: Alex Bodurka, Portage, MI (US); Jan H. Ettrich, Geneva, IL (US); David Toll, Cicero, IN (US)

(73) Assignee: MASONITE CORPORATION, Tampa, FL (US)

( * ) Notice: Subject to any disclaimer, the term of this patent is extended or adjusted under 35 U.S.C. 154(b) by 0 days.

(21) Appl. No.: 17/473,492

(22) Filed: Sep. 13, 2021

Related U.S. Application Data

(60) Provisional application No. 63/077,193, filed on Sep. 11, 2020.

(51) Int. Cl.
G07C 9/27 (2020.01)
G07C 9/10 (2020.01)
G07C 9/25 (2020.01)
G16H 10/20 (2018.01)

(52) U.S. Cl.
CPC .............. G07C 9/27 (2020.01); G07C 9/10 (2020.01); G07C 9/25 (2020.01); G16H 10/20 (2018.01)

(58) Field of Classification Search
CPC .............. G07C 9/27; G07C 9/25; G07C 9/10
See application file for complete search history.

(56) References Cited

U.S. PATENT DOCUMENTS

| | | | |
|---|---|---|---|
| 10,832,509 B1 * | 11/2020 | Read | H04W 12/06 |
| 2021/0375084 A1 * | 12/2021 | Aubrey | G07C 9/27 |
| 2022/0068070 A1 * | 3/2022 | Ouellette | G07C 9/30 |

* cited by examiner

*Primary Examiner* — Nabil H Syed
(74) *Attorney, Agent, or Firm* — Cantor Colburn LLP

(57) ABSTRACT

An entry system includes a plurality of first user devices, such as key fobs, ID cards and the like. A plurality of second user devices are maintained by users, and may include mobile phones, smart watches and tablets. A main entry system controls a barrier to allow entry to approved individuals. An authorization system is configured to validate the first and second user devices, and to send an electronic questionnaire to the second user device. The user must complete the questionnaire and transmit it to the main entry system. The second user device, the main entry system, and the authorization system communicate with each other over a computer network. If the user successfully completes the questionnaire and the user's identity is authenticated, the main entry system allows the barrier to be opened so that the user may enter the facility.

18 Claims, 29 Drawing Sheets

ENTRY ACCESS SYSTEM AND METHOD WITH QUESTIONNAIRE SCREENING

CROSS-REFERENCE TO RELATED APPLICATIONS AND CLAIM TO PRIORITY

This application claims the priority of U.S. Provisional Patent Application No. 63/077,193, filed Sep. 11, 2020, which is incorporated herein by reference.

FIELD OF THE INVENTION

The present invention relates to entry systems and methods containing identity verification and survey information, such as a wellness survey, security verification questionnaire, and the like, to control access to a buildings, secure areas or the like.

BACKGROUND OF THE INVENTION

With many contagious diseases isolation and social distancing are the most effective means to prevent the spread of the disease. For some diseases, such as COVID 19, a questionnaire may provide a rough indication of the risk of a person having the disease. For example, with COVID 19, contact with a disease positive individual, fever, respiratory symptoms, etc. may indicate that the person may have the disease. As such, office buildings sometimes question people for symptoms/risks of the disease to decide whether to allow entry. The entrants are usually required to answer the questionnaire at the door, either by a guard asking the questions or by filling out a form that is then reviewed before access is allowed. The process sometimes results in long lines at the door due to the time it takes to process the questionnaires.

Many buildings, such as office buildings or factories, already have entry systems which verify the identity of entrants before allowing entry, such as for security purposes. Such buildings would benefit from integrating a wellness questionnaire into the entry system, provided that long lines at the entrance were avoided. Therefore, there is a need for an entry system that provides identity verification as well as health screening monitoring and monitoring for regulatory, compliance and corporate governance of entrants prior to their entry into the building space.

Access to some buildings and facilities is sometimes limited for security and all regulatory requirements to individuals who have a certain credential that permit access. The credentials may be valid for a limited period, thus requiring periodic verification. Keeping track of individuals and whether they have the required credentials can be a laborious task, sometimes resulting a lines of individuals seeking access to a building or facility.

A system and method that keeps a record of individuals accessing a building or facility and also whether they have the necessary credentials in a time-saving manner is desirable in order to expedite entry and provide positive verification of who accessed the building or facility should the need arise.

SUMMARY OF THE INVENTION

The present invention provides an entry system for controlling access to a secure space, such as a building. In particular the entry system provides identity verification or authentication, preferably multifactor identification, and a questionnaire/survey to control access to a building, secure area or the like. The questionnaire/survey may be used for health screening or to assure that individuals enter the secure space in a manner that assures regulatory compliance and/or compliance with internal corporate governance.

The entry system includes several components, such as a main entry system, a verification system, and a plurality of user devices that interact with the main entry and verification systems. The components preferably communicate with each other wirelessly to control access to the secure space.

Methods for making and using the different aspects of the present invention are also provided.

Other aspects of the invention, including apparatus, devices, kits, processes, and the like which constitute part of the invention, will become more apparent upon reading the following detailed description of the exemplary embodiments

BRIEF DESCRIPTION OF THE DRAWINGS

The following detailed description of the invention will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE PREFERRED EMBODIMENTS

Figure 1:
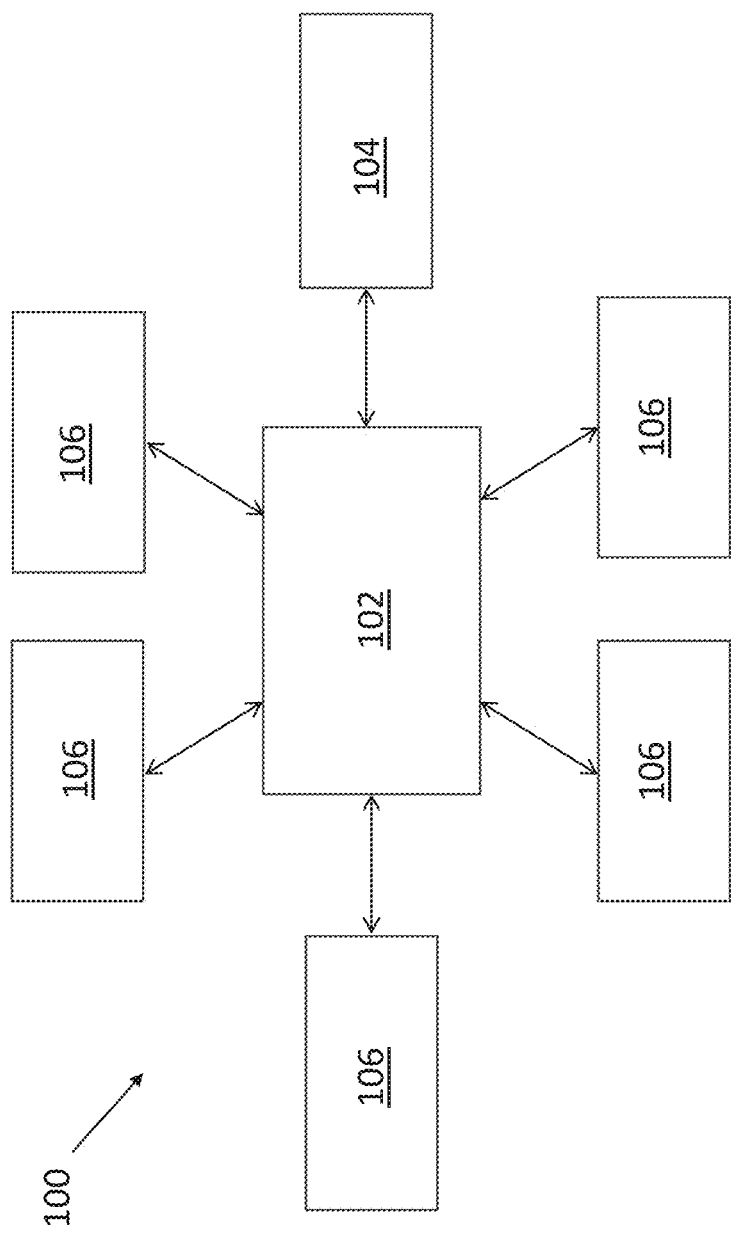
FIG. 1 is a schematic of the entry system of the present invention.

Reference will now be made in detail to exemplary embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in connection with the exemplary embodiments and methods.

The present invention relates to entry systems for allowing entry into a secure space, such as an office building, a factory, a manufacturing facility, etc. Referring to FIG. 1, the entry system 100, preferably an automated system provided with a hardware and software platform, includes a main system 102 in electronic communication with an identity verification system 104 for verifying the identity of the building entrants, and interfacing with a plurality of user devices 106, such as fob keys, smartphones, tablets, watches and the like.

Figure 2:
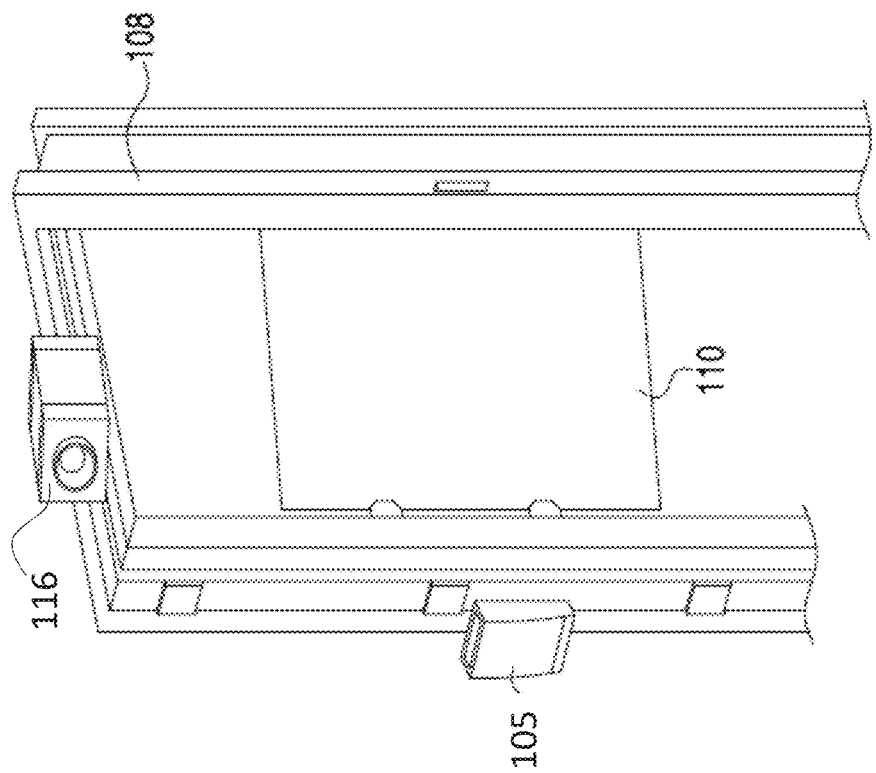
FIG. 2 is a perspective view of an exemplary entranceway.

Part of the identity verification system 104, preferably includes a verification device 105, as shown in FIG. 2, that may be located at the entrance to the secure space, such as the entrance to a building, laboratory, etc. The entrance may include a frame 108 mounted to a wall around the entrance, and a barrier, such as a door, 110 pivotally or movably mounted on the frame 108. The verification device 105 may be mounted to the frame or the barrier 110. The barrier 110 can partially or completely cover the frame opening (FIG. 2 shows the barrier 110 partially covering the frame opening) and can be, but is not limited to, a door, a gate, a bar, a curtain, a turnstile, or combinations thereof. Other visual or physical restraints may also be appropriate for the present invention.

The identity verification device 105 may be, but is not limited to, an RFID reader, a fingerprint scanner, a retinal scanner, a camera, a keypad, a writing pad, a voice recorder, a bar code reader, a QR reader or combinations thereof. Identity (ID) verification may, e.g., include the capability of capturing images or data from or about individuals, and of comparing the image or data to data within existing internal databases or third-party databases for identity matches. ID verification may be capable of capturing images of a user/person, or reading his/her identification card, employee badge, a bar code, a QR code, etc., and then cross referencing the images with the database of a third-party access control system (ACS). A photo of a person may be analyzed by a facial recognition algorithm to compare it against a database of images. Upon a match in the data or a positive identification of the individual person, the system may allow the person to enter the secure space.

In another embodiment, multi-factor verification may be used to improve the reliability of ID verification. Multi-factor verification or multi-factor authentication may be accomplished by requiring a user's entry privileges to be authenticated by using more than just a simple key card. At many secure facilities, users are provided with access badges to swipe against door readers to enter restricted areas. One problem with such access control is that anyone that has access to the badge can improperly gain access to the restricted area. Multi-factor verification minimizes this problem by validating the identity of the user that is requesting access twice, e.g., once with a key card or the like, and then a second time with facial recognition, fingerprints, iris scan, face/voice recognition, signature, or personal identification number.

A user device 106, such as a smart phone, a smart watch, or a tablet is to be associated with the user. The user device 106 is provided with a hardware and software platform for electronic communication with the main system 102. The user device 106 preferably communicates wirelessly with the main system 102. The user device 106 communicates with the user interface electronically through electronic communication devices that may include sensors, gateways, switches, routers, hubs or any other electronic communication device to the remotely located main system 102. The user device 106 may transmit its information, e.g., location and identity of the user, on an ongoing basis or intermittently (preferably intermittently), directly to the main system 102 or via the other electronic communication devices. Preferably, the user device 106 communicates with the main system 102 only when the user device is within specified areas (as discussed below). The communication preferably uses wireless technologies and protocols for electronic communication such as cellular (3G/4G/5G), Bluetooth, Bluetooth Low Energy, WiFi, TCP/IP, near field communication (NFC), and other such technologies and protocols.

Figure 3:
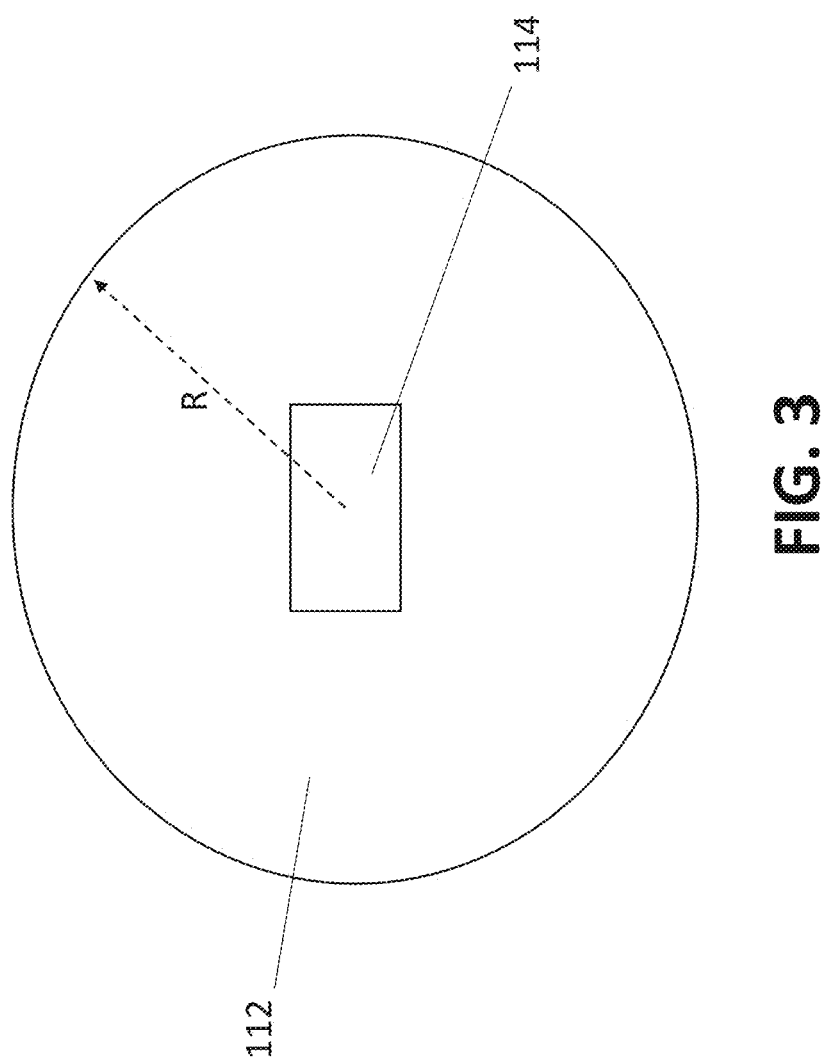
FIG. 3 is a diagram illustrating the entranceway of FIG. 2 with geofencing technology.

In a preferred embodiment, geofencing may be used to trigger a push notification to the user device 106 advising the user to fill out a questionnaire before attempting to enter the secure space. The user device 106 communicates its location information to the main system 102 on some basis, such as periodic or intermittent. Referring to FIG. 3, when the transmitted location is within a specified location or area 112 relative to the secure location 114, the main system 102 is notified. The specified location 112 may be set in advance in the main system 102, and may be, e.g., the parking lot of the secure space 114 and/or a specified distance from the secure space 114. For example, as shown in FIG. 3, the specified location may be an area within a radius R from the center of the secure space 114. When a user is within the specified location 112, as determined by the location of the user device 106, the main system 102 sends a push notification to the user to fill out the questionnaire. The user may be instructed to log in to a website to answer the questionnaire or to answer the questionnaire sent directly to the user device. Once the questionnaire is completed, it, along with the user identity information, is forwarded to the main system 102.

In case of COVID-19, the questionnaire includes questions relating to risk factors indicating high risk of contracting the disease or symptoms of the disease. Of the symptoms, the questions may ask whether the user has one or more of the following symptoms:
- Fever or chills
- Cough
- Shortness of breath or difficulty breathing
- Fatigue
- Muscle or body aches
- Headache
- New loss of taste or smell
- Sore throat
- Congestion or runny nose
- Nausea or vomiting
- Diarrhea
- Loss of smell or taste Other the risk factors include whether the user has
- Been tested for the disease
- Been diagnosed with disease
- Been in contact with a person with disease within the last 14 days
- Travelled to any regions affected by disease within the last 14 days Underlying health conditions, such as heart disease, lung disease, kidney disease, diabetes, autoimmune disorders, etc.

Other diseases, including other infectious diseases, mental health, or overall wellness, may also be similarly screened using similar questionnaires with risk factors and symptoms associated with that disease. The questionnaire may inquire about the user's mental state (angry/sad/happy), stress, or other conditions. For infectious diseases, the user should access the questionnaire before requesting entry to the secure space 114. For general wellness and mental health, the user should access the questionnaire periodically, once a week or once a quarter.

While we disclose use of the system 100 for health screening, it may be used to assure that individuals enter in a manner that assures regulatory compliance and compliance with internal corporate governance. The system 100 utilizes observed data (biometrics) and user-provided data to determine whether to perform some action, such as allow access, track wellbeing, provide a notification, etc. Security regulations may, for example, preclude entrance where an individual has visited a country or region within a period of time. Corporate governance may preclude entrance until an entrant has signed a non-disclosure agreement (NDA). The system 100 allows multiple types of questionnaires to be provided to a proposed entrant in order to assure compliance with health, regulatory and corporate governance protocols. Regulatory and corporate governance may include updating or providing appropriate non-disclosure agreements (NDAs), security clearance, safety protocols, codes of conduct, non-compete, engagement census, and other re-accruing processes that require acknowledgment or feedback from employees or visitors.

In additional to the questionnaire, the system 100 may include one or more sensors 116 (FIG. 2), such as a temperature sensor, a camera, other the like. For example, the sensor 116 may be a temperature sensor to detect body temperature of the user. Alternatively, the sensor 116 may be a camera with associated software to detect the user's facial features to determine the user mood (angry/sad/happy).

Once transmitted to the main system 102, the questionnaire is valid only for a selected amount of time. For example, the selected amount of time may be 10 minutes or less, 5 minutes or less, preferably about 2 minutes. The selected amount of time is preferably calculated to allow the user to arrive at the entrance of the secure area to request entry. While health screening may require that the period during which a questionnaire response is valid is relatively short, other protocols, such as for regulatory and corporate governance may allow a much longer period, such as a calendar quarter or possibly longer. After the selected amount of time has passed, the answered questionnaire expires. If the user is still in or near the specified location 112, the main system 102 notifies the user device 106 of the expiration and requests that another questionnaire be completed. Alternatively, the main system 102 may notify the user device 106 that the questionnaire is expiring and request that the user affirmatively extend the expiration.

Operation of the entry system 100 is described in the following. When the user is within the specified location 112, the user device 106 notifies the main system 102, e.g., via an application installed on the user device 106 that is in communication with the main system 102. The user is then advised to fill out the questionnaire. Alternatively, the user may fill out the questionnaire before leaving for the secure space 114. One advantage of filling out the questionnaire before leaving is that the user is informed whether he/she is cleared for entry before having to drive all the way to the secure space 114. Once completed, the questionnaire and user information are transmitted to the main system 102. Preferably, if the questionnaire is not cleared, the user is immediately notified that entry will not be permitted. When the user first requests entry into the secure space 114 and presents his/her credential, such as a badge containing an RFID chip, the identify verification device 104 reads the badge or other credential and confirms the identity of the user. At the same time, the main system 102 confirms whether the user has filled out the questionnaire. The person's authorization to enter is validated only when the person's identity and questionnaire are cleared. Once validated, the person is granted access and entry to the secure space 114. To be granted access to the secure space 114, the person's identity must be verified, and the questionnaire must be cleared, i.e., no risk or symptom of COVID-19 (or other infectious disease). If one or more of the symptoms or one or more risk factor are present, entry may be denied. If entry is denied, in certain embodiments, a receptionist/attendant/healthcare professional is called to perform further testing, perform further questioning, and/or to reschedule entry for a later time. The receptionist/attendant/healthcare professional may meet the user at the entrance to the secure space 114 or contact the user at a later time.

When epidemic disease condition is not prevalent, the system 100 may be used to monitor the user general wellbeing. For example, the system 100 may be used to detect the individual's general wellness. If unwell conditions are detected by the system 100, reminders may be sent to the user to take a day off and/or to seek healthcare.

Figure 4:
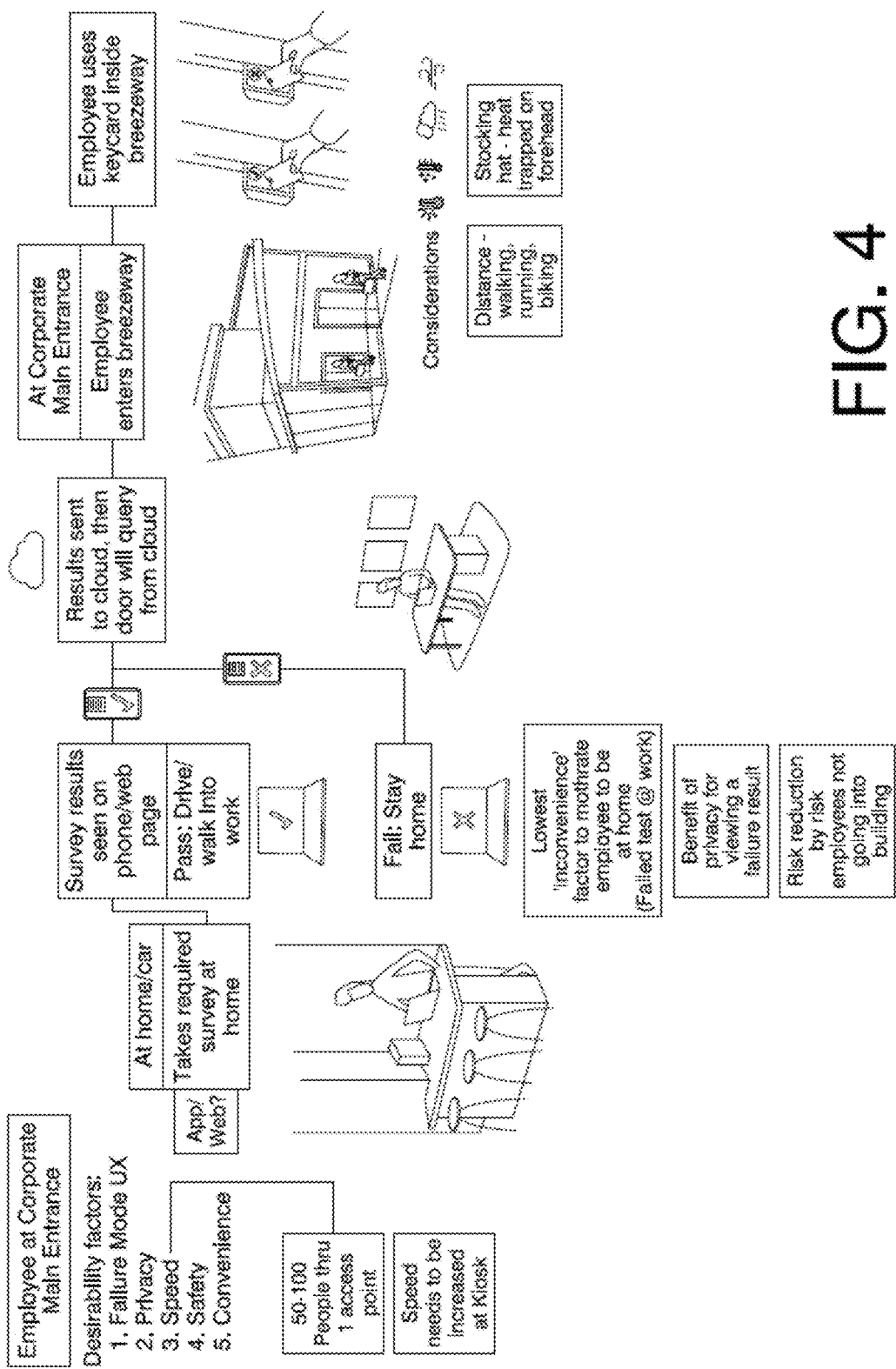
FIG. 4 is a flow diagram showing the system as configured for use during an epidemic to control access by a user (employee) at a main entrance.
Figure 5:
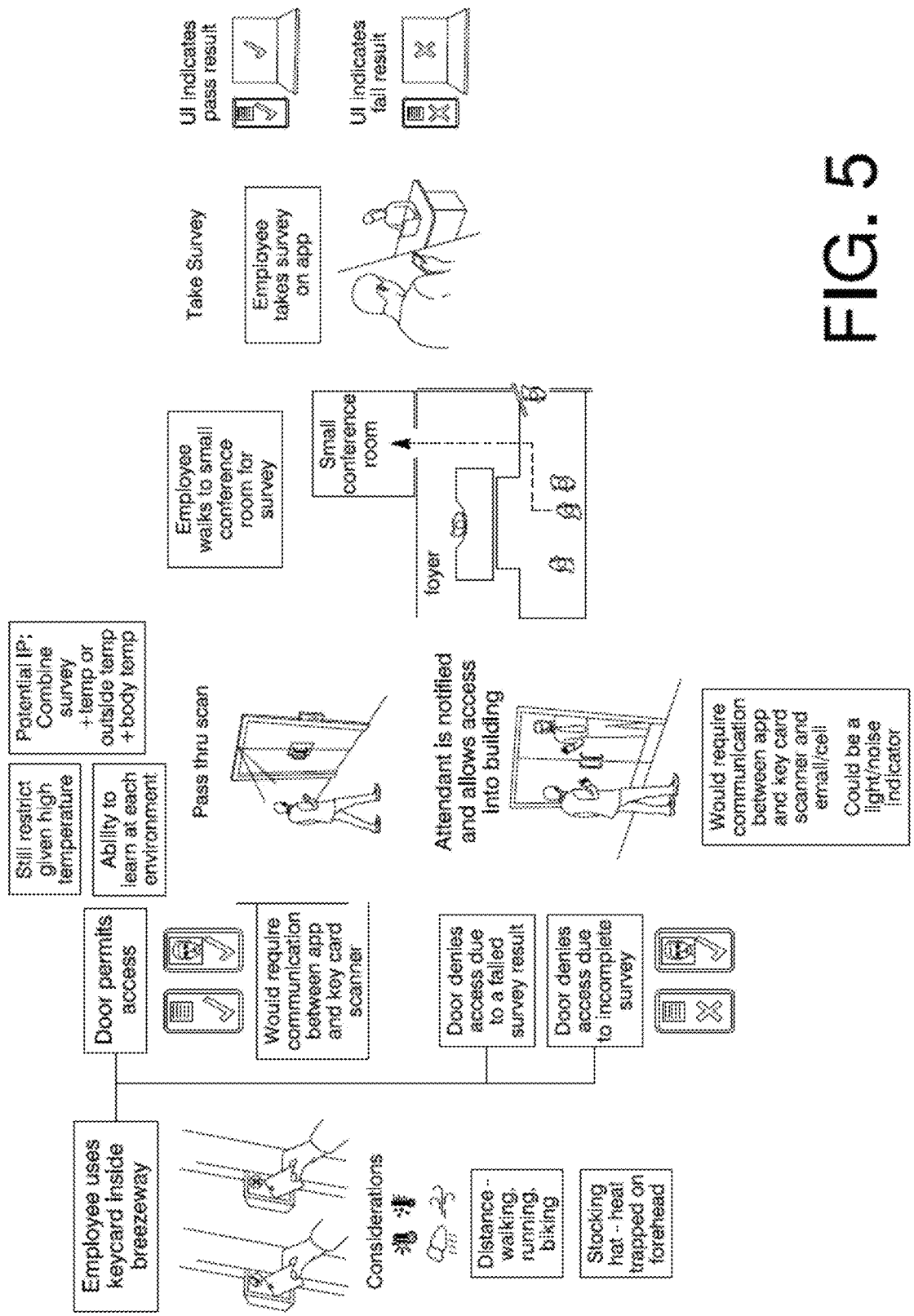
FIG. 5 is a continuation of the flow diagram of FIG. 4.

FIGS. 4-5 illustrate use of the system 100 when an employee wishes to access the main entrance of the office or like work facility. In that event, the employee/user may take the survey from home and access to the facility will be permitted when the survey is successful and a key card or like identifier swiped at the entrance determines the identity of the employee and that the employee has successfully passed the survey. If the survey has failed, then access is denied.

Figure 6:
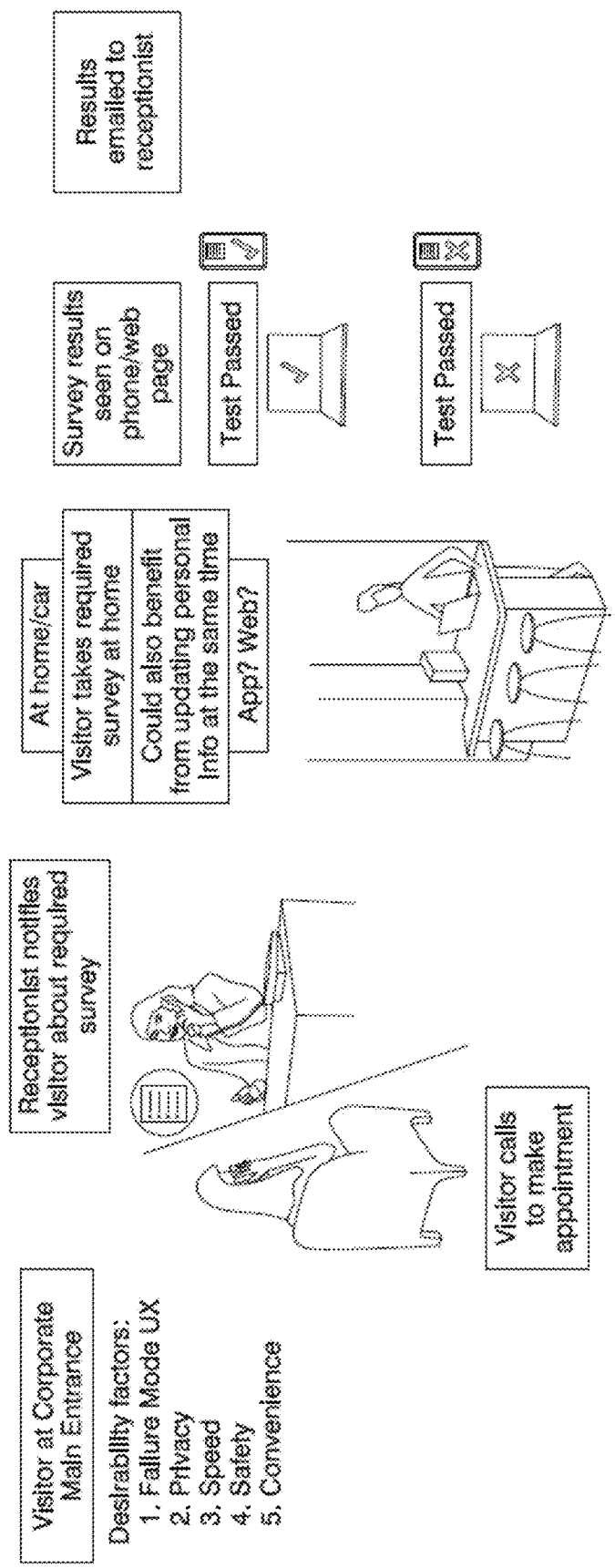
FIG. 6 is a flow diagram showing the system configured for use (to monitor general wellness or a specific disease or condition) to control access by a user (visitor) at a main entrance.
Figure 7:
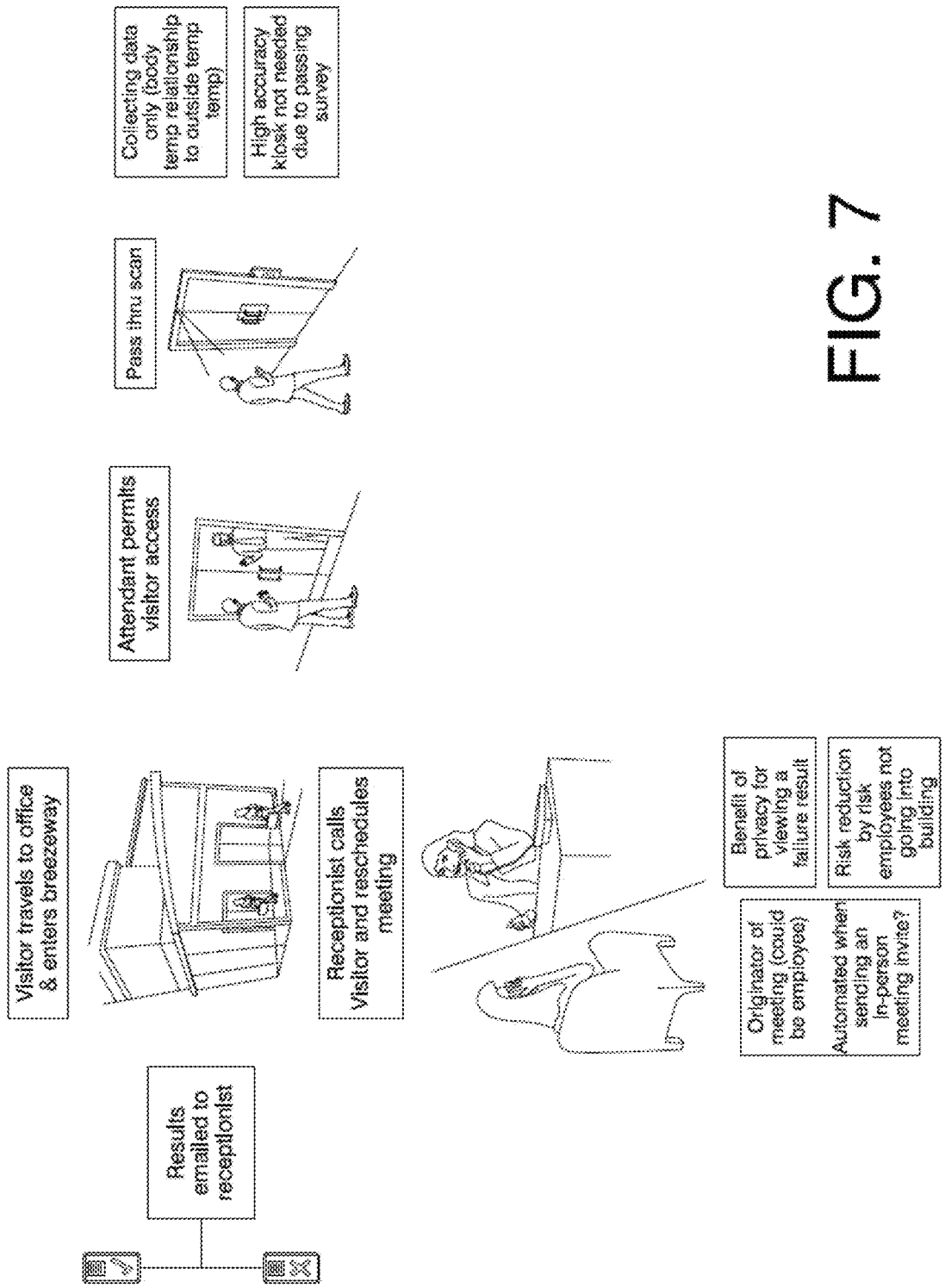
FIG. 7 is a continuation of the flow diagram of FIG. 6.

FIGS. 6-7 illustrate use of the system 100 when a visitor seeks to access the facility. In that event, the visitor's identity is first determined, such as by presentation of a valid driver's license or other government identification card, and then the survey completed successfully prior to access being allowed.

Figure 8:
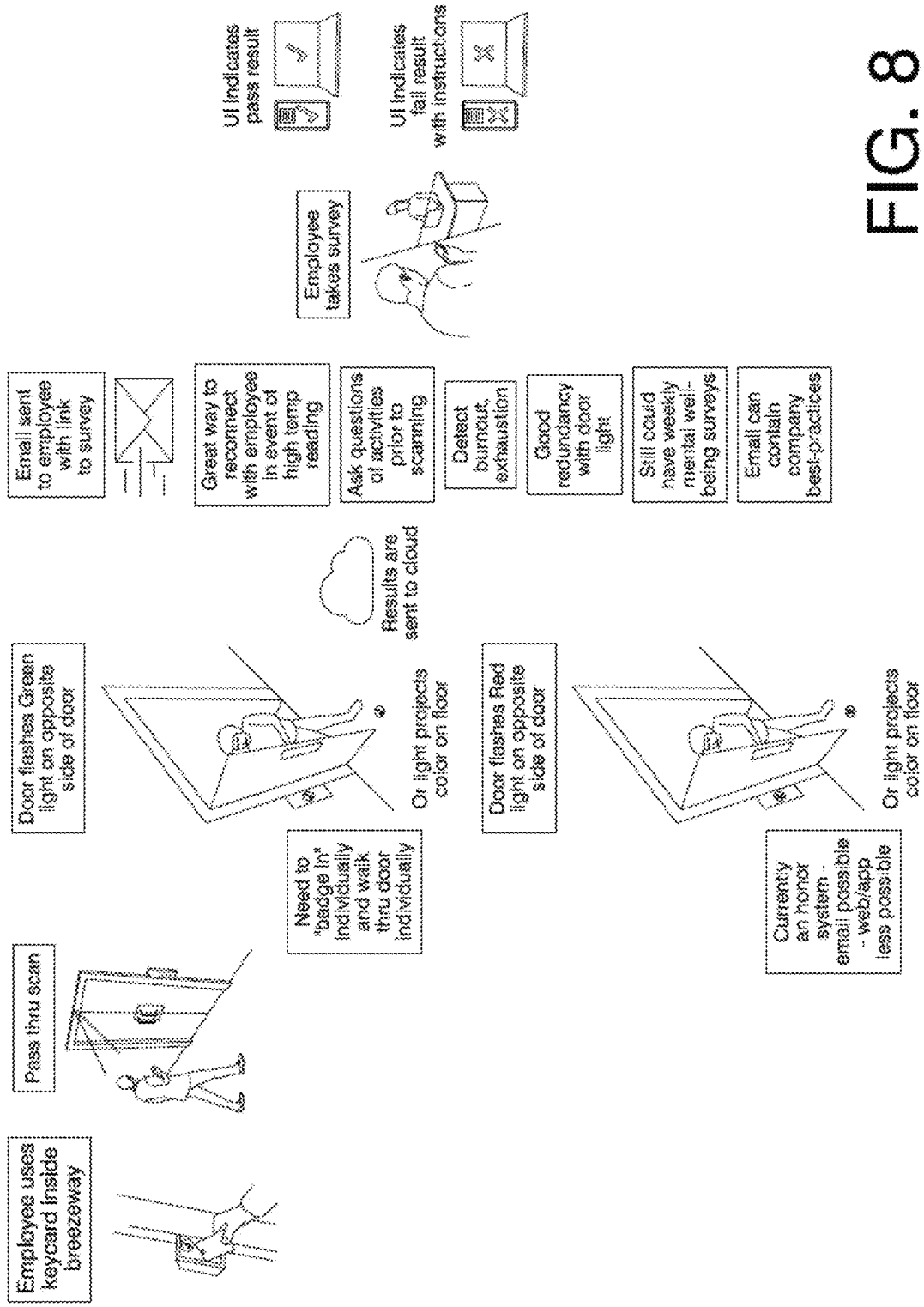
FIG. 8 is a diagram showing the system configured for use to monitor a user's (employee's) general wellness and to control access by the user at a main entrance.
Figure 9:
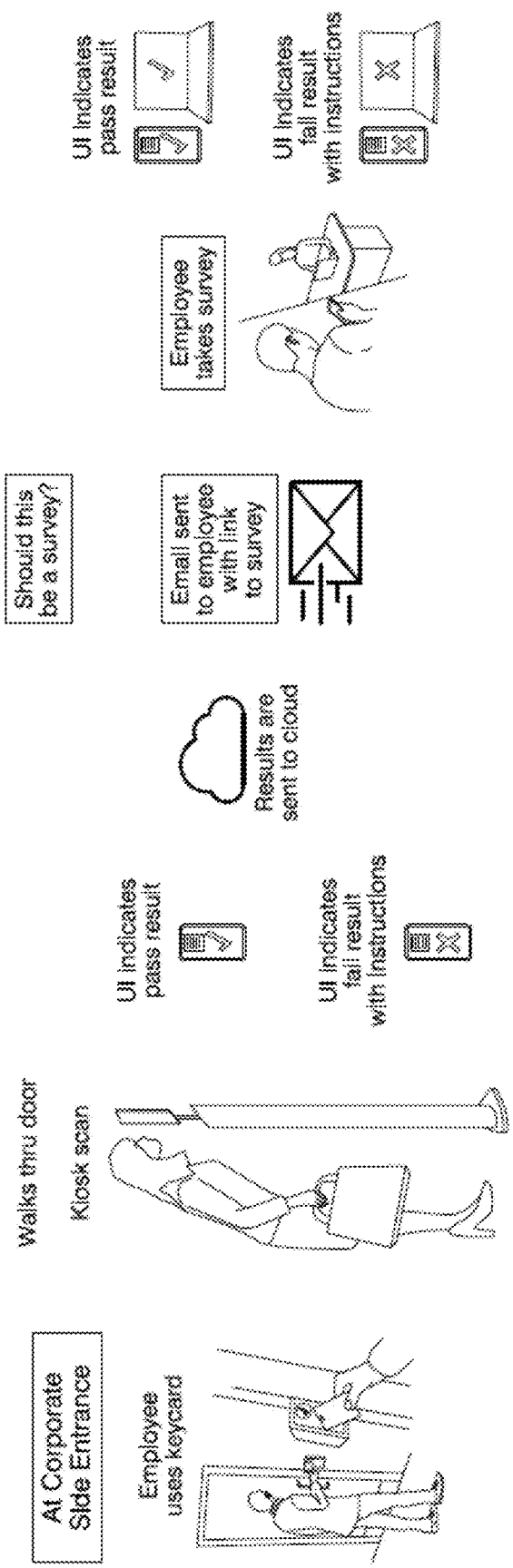
FIG. 9 is a diagram showing the system configured for use to monitor a user's (employee's) general wellness and to control access by the user at a side entrance.

FIGS. 8-9 illustrate use of the system 100 when being used to monitor the general wellness of employees. The operation is similar to FIGS. 4-5, except that the survey questions relate to the general well-being of the individual and are not directed to a particular disease.

Figure 10:
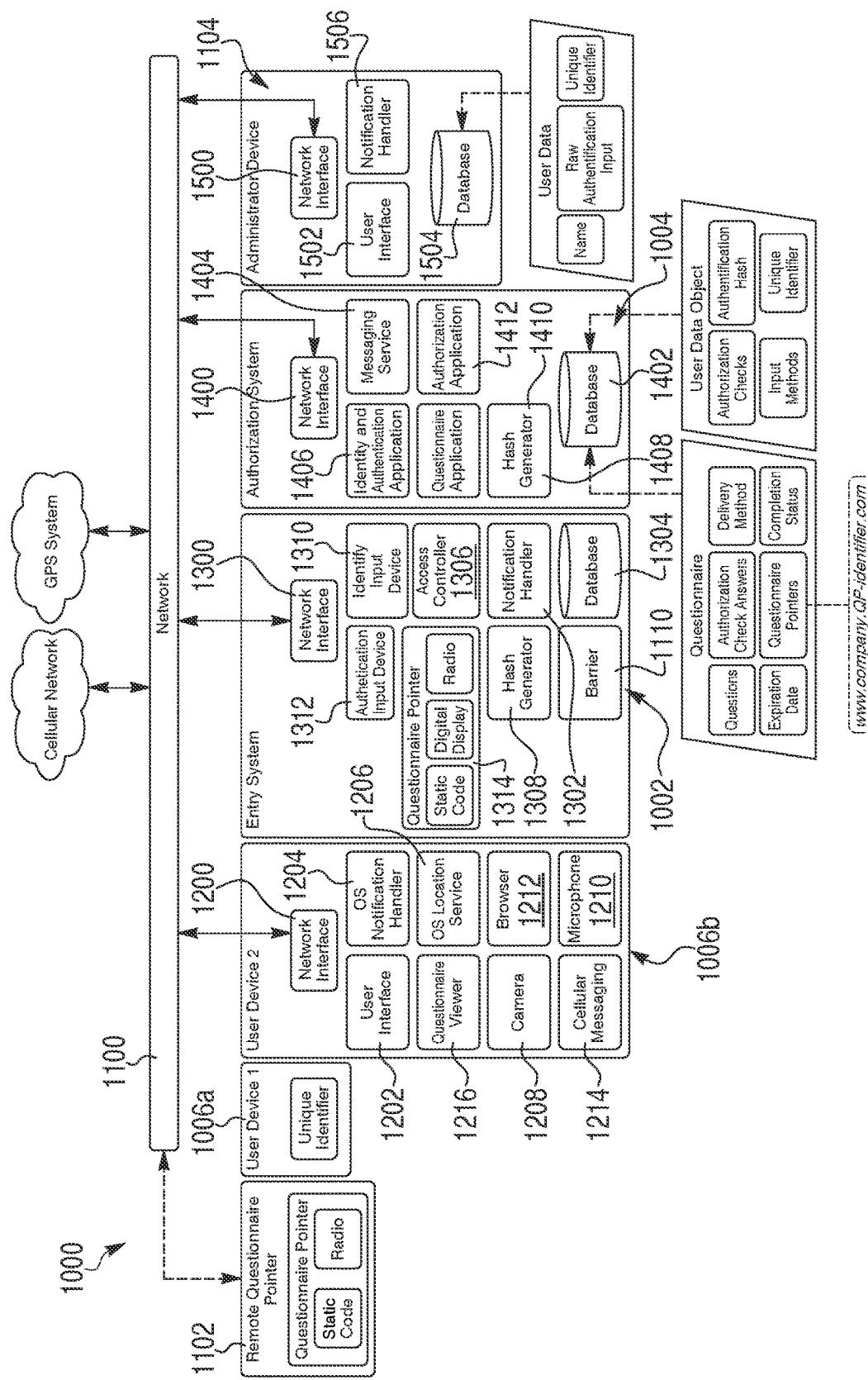
FIG. 10 is a diagram showing an exemplary entry system.
Figure 11:
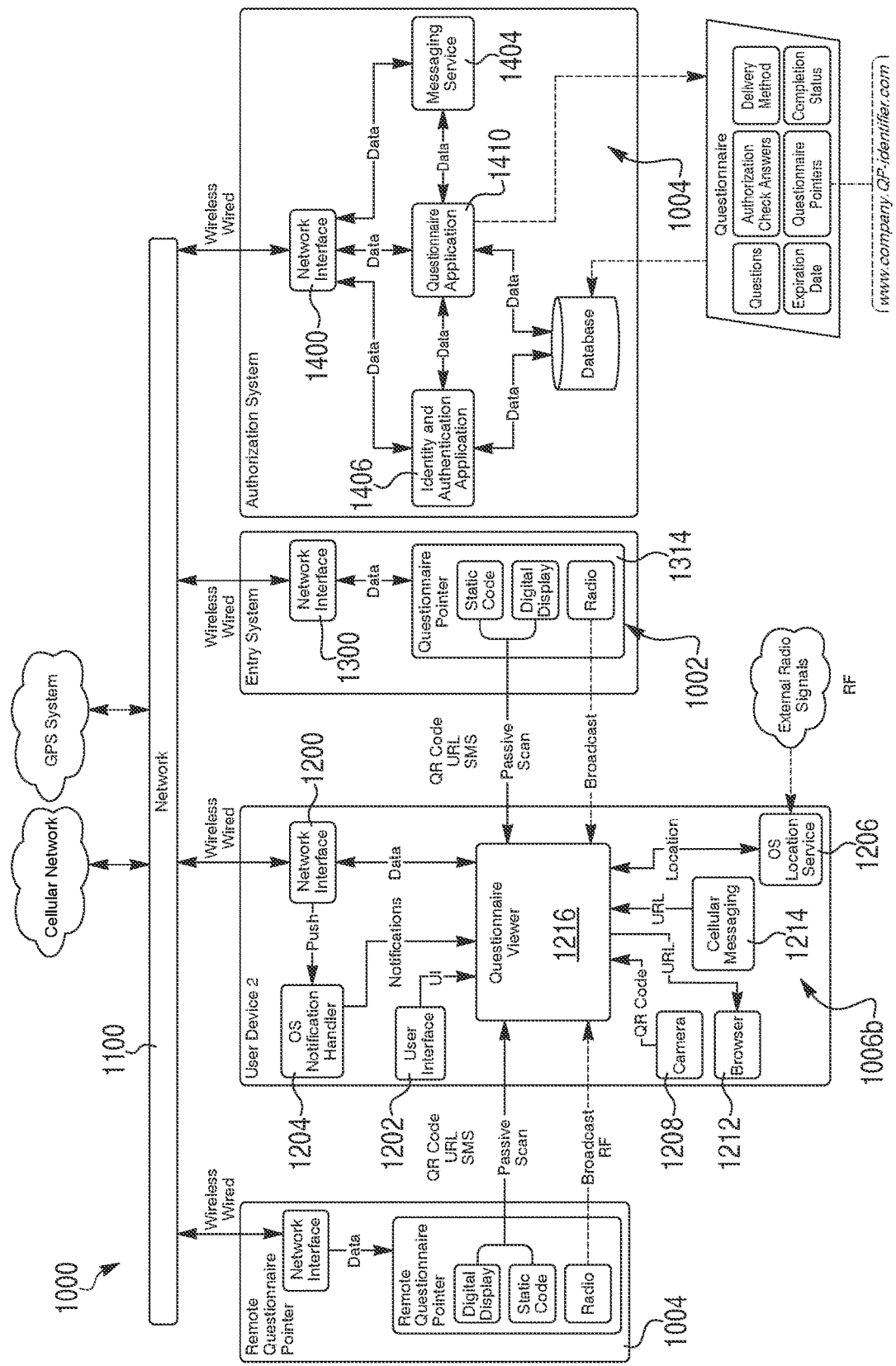
FIG. 11 is a diagram showing the data flow in the exemplary entry system for questionnaire delivery.

FIG. 10 shows an exemplary entry system 1000 of the present invention utilizing multifactor verification. The system 1000 includes a network 1100 operating over cellular, WiFi, and/or wired Ethernet networks and GPS system. The system 1000 includes first user devices 1006a, second user devices 1006b, a main entry system 1002, a verification (or authorization) system 1004, and an administrator device 1104. FIG. 11 shows the communication and data flow of the system 1000.

The network 1100 preferably uses wireless technologies and protocols for electronic communication such as cellular (3G/4G/5G), Bluetooth, Bluetooth Low Energy, WiFi, TCP/IP, near field communication (NFC), and other such technologies and protocols. Preferably, the network 1100 also provided with location information from the second user device 1006b via the GPS on the second user device 1006b. The components of the system communicate with each other via the network 1100.

The system 1000 preferably uses two user devices 1006a and 1006b for two-factor authentication. The first user device 1006a may preferably be, but not limited to, a FOB key, a card key, or other devices using RFID technology, for example, to enter a building. The first user device 1006a need not interface with the network 1100, as it may be read by the verification system 1004 at the entrance to the secure space 114 or on the pathway to the secured space 114. Preferably, the first user device 1006a provides a unique identifier for every user, so that the main entry system 1002, on reading the first user device 1006a, identifies the first user device 1006a as associating with a particular user.

The second user device 1006b may preferably be a smart phone, a smart watch, laptop, or a tablet associated with the user. The second user device 1006b preferably includes one or more of the following modules: a network interface 1200, a user interface 1202, an operating system (OS) notification handler 1204, a location service 1206, a camera 1208, a microphone 1210, a browser 1212, a cellular messenger 1214, and a questionnaire viewer application 1216. A typical smart phone typically includes all of those modules.

The network interface 1200 interfaces the second user device 1006b to the network 1100 wirelessly, such as by cellular, WiFi, and/or wired Ethernet networks, and is usually provided by the operating system of the second user device 1006b. The network interface 1200 is used by the device 1006b to communicate with the main entry system 1002 and the verification system 1004 via the network 1100.

The user interface 1202 is preferably provided by the OS of the second user device 1006b and provides a platform for the user to input information to applications running on the second user device 1006b.

The notification handler 1204 is provided by the OS of the second user device 1006b and handles the receiving and presentation of push notifications to the device 1006b (see FIG. 11). The notification handler 1204 is used by the questionnaire viewer 1216 to let the user know he/she has a questionnaire to fill out (see FIG. 11).

The Location Service 1206 provides location information to applications running on the second user device 1006b. It is preferably provided by the second user device 1006b and may use GPS, WiFi, Bluetooth, and other triangulation methods for providing the location of the second user device 1006b. The questionnaire viewer 1216 preferably uses this location service 1206 in two ways: 1) to automatically present the user with a questionnaire based on the location or proximity to an entry system; and 2) to use the location service 1206 as an authentication input as it provides additional assurance that a particular user is the one who is attempting to gain access (multifactor authentication).

The camera 1208 is preferably provided by the second user device 1006b and operable via the device's OS. The user may use the camera 1208 to scan a QR Code to launch a questionnaire. Additionally, the questionnaire viewer 1216 can also use the camera 1208 to provide an authentication input in the form of an image of the user's face, e.g., for facial recognition for use in multifactor authentication (see FIG. 11).

The microphone 1210 is preferably provided by the second user device 1006b and operable on the device's OS. The questionnaire viewer 1216 can also use this to provide an authentication input in the form of a recording of the user's voice, e.g., for voice recognition for use in multifactor authentication.

The browser 1212 is preferably provided by the second user device 1006b and operable on the device's OS. This browser can be used by the user to fill out the questionnaire.

The cellular messenger 1214 may be a text message (a.k.a. SMS) service provided by the second user device 1006b and operably on the device's OS. A user may use this cellular messenger 1214 to request a URL to a questionnaire from the system 1000.

The questionnaire viewer 1216 is preferably an application on the second user device 1006b that the user uses for filling out and managing questionnaires. It can also configure the OS to provide notifications and location tracking used by the questionnaire viewer 1216 to automatically present users with the questionnaire.

The main entry system 1002 allows entry into the secure space 114. It preferably includes processors and associated electronics that are purpose-built for the application, such as the access controller, questinare pointer, notification handler as explained below; however, off-the-shelf electronic components, such as the barrier, authentaction input device, identity input device, network interface, and database as explained below, may be included. The main entry system 1002 preferably includes one or more of the following modules: a network interface 1300, a notification handler 1302, a database 1304, a barrier 1110, an access controller 1306, a hash generator 1308, an identity input device 1310, and an authentication input device 1312.

The network interface 1300 interfaces the main entry system 1002 to the network 1100 wirelessly, such as by cellular, WiFi, and/or wired Ethernet networks. The network interface 1300 allows the main entry system 1002 to communicate with the network 1100, and thereby, with the second user device 1200 and the verification system 1004.

The notification handler 1302 allows the main entry system 1002 to provide user feedback (i.e., notifications). These notifications may provide reminders to the user of actions need by the user. For example, the notifications may let the user know that a questionnaire will expire in the near future or has expired but is not needed for access. Additionally, for health screening, the notifications may indicate to the user whether he/she has a health metric that is out of the normal range. Other notification actions may be providing an NDA, additional security clearance, health screening, safety protocols, codes of conduct, non-compete, engagement census, or other re-accruing processes that require acknowledgment or feedback from employees or visitors.

The database 1304 is a storage device used by the access controller 1306 to store system configuration data, history logs, user data objects, and other data required for proper operation.

The barrier 1110 provides a physical barrier used to grant and restrict access to the secure space 114. A typical barrier 1110 is a door having a latch for locking and unlocking of the door. The access controller 1306 electronically controls the locking and unlocking of the latch to allow or restrict access to the secure space 114 via the barrier 1110.

The access controller 1306 is preferably an electronic device equipped with a processor, memory, storage, and software application(s). The access controller 1306 receives local inputs from the authentication input device 1312 and the identity input device 1310. In addition, the access controller 1306 communicates with other devices on the network via the network interface 1300. The access controller 1306 is responsible for controlling the barrier 1110 which controls access to a physical space. Furthermore, the access controller 1306 may be used to control the QP 1004 and notification handler 1302.

The hash generator 1308 (a.k.a. hashing function, cryptographic hashing algorithm) is used to convert and securely store sensitive biometric (e.g., facial imagery and voice) data. The hash generator converts data of an arbitrary size to data of a fixed size. This compresses the data to significantly reduce the amount of storage required to store the data. It also reduces the amount of data that has to be shared over the network 1100. A cryptographic hash algorithm for the hash generator provides additional security and privacy benefits since the user's raw biometric data is never stored. The hash generator 1308 may be a separate module (as shown in FIG. 10) or on the same electronic board as the access controller 1306.

The identity input device 1310 is used to capture the identity input from the user. A preferred implementation involves an RFID scanner for reading the first user device 1006*a* or a keypad for entry of an entry code (e.g., a combination of letters and/or numbers uniquely assigned to the user) from the user. This input is then sent to the access controller 1306.

The authentication input device 1312 captures an authentication input from a user. The authentication input device 1312 may include a digital camera and/or a microphone that can be enabled/disabled by the system administrator via the configuration of the system, e.g., for multi-factor authentication. The authentication input device 1312 captures raw imagery of a user's face and/or voice, which are sent to the access controller 1306 and eventually to the authorization system 1004 to authenticate a user through facial or voice recognition as explained below.

The questionnaire pointer (QP) 1314 is a sign or display, preferably controlled by the access controller 1306 and provides a link to a questionnaire required for accessing the building. The QP 1314 preferably provides a URL link to a questionnaire/survey/form that the user must fill out before entry into the secure space 114. The QP is preferably an electronic sign that provides the URL link by providing a QR Code or phone number for receiving the URL via text message. Additionally, the QP 1314 can be used for authentication purpose. The QP 1314 preferably includes three modules: a digital display, a static code (e.g., a non-digital sign), and a radio. The digital display allows the main entry system 1002 to display text and imagery that are electronically sent from the access controller 1306. When used for delivering a questionnaire to a user, the display can be configured to display a QR Code, URL, or phone number (see FIG. 11). These allow the user to access the questionnaire/survey/form that the user is required to complete, preferably via the second user device 1006*b*. When used for authentication purposes, the digital display can provide a one-time-use alphanumeric value to the user. The user would then use the questionnaire viewer 1216 on the second user device 1006*b* to enter this value. Providing a correct alphanumeric value authenticates that a particular user is attempting to use a specific entry system at a particular point in time.

The static code is used to provide a URL link to a questionnaire/survey that visitors of a building must fill out before entry. The QP 1314 can provide the URL link by giving a static QR Code or phone number for receiving the URL via text sent to the second user device 1006*b*. The radio is electronically controlled by the access controller 1306. When used for delivering a questionnaire to a user, the radio can broadcast a URL that can be scanned by a user's phone. This can be done via Bluetooth, Bluetooth Beacons, or NFC. Additionally, the radio may be a WiFi radio, which is configured as an access point with no password required. However, when the user attempts to join the network, the user is presented with a questionnaire instead of a login screen. Once the user submits the questionnaire, the user's device will be removed from the network (the user cannot use this network to connect to the internet). When used for authentication purposes (multifactor authentication), the radio can be used to determine whether the second user device 1006*b* is within close proximity, preferably less than about 100 m, more preferably less than about 50 m, most preferably less than about 20 m to the barrier 1110 where the identity code is entered by the user. In this scenario, the radio broadcasts itself to be scanned by the second user device 1006*b* via the questionnaire viewer 1216. The questionnaire viewer 1216 then sends this information (whether the second user device 1006*b* is proximate to the barrier 1110) to the authorization system 1004. If the second user device is indeed proximate to the barrier 1110, the authorization system 1004 authenticates the user who entered the identity input information into the main entry system 1002.

The verification system (authorization system) 1004 preferably includes one or more servers that can be installed on-premise or remotely. For latency concerns, local installation is preferred. However, a remote server may provide a less expensive alternative. The authorization system 1004 is used for hosting, managing, and configuring a questionnaire application 1410 located thereon. Additionally, the system determines whether a particular user is authorized to enter a building or area within a building. The authorization system 1004 verifies the identity and authentication inputs that the user presented to the main entry system 1002 and/or the second user device 1006*b*. Furthermore, the authorization system 1004 may require the user to submit a questionnaire before authorizing access by the user. The authorization system 1004 takes the user's inputs and determines whether or not the user has presented the correct information to be authorized for access. The authorization system 1004 preferably includes one or more of the following modules: a network interface 1400, a database 1402, a messaging service 1404, an identity and authentication application (IAA) 1406, a hash generator 1408, the questionnaire application 1410, and an authorization application 1412.

The network interface 1400 interfaces the authorization system 1004 to the network 1100 wirelessly, such as by cellular, WiFi, and/or wired Ethernet networks. This network interface 1300 allows the authorization system 1004 to communicate with the network 1100, and thereby, with the second user device 1006*b* and the access controller 1306 on the main entry system 1002.

The database 1402 is a storage device used by the authorization system 1004 to store system configuration data, history logs, user data objects, questionnaires, questionnaire submissions, and other data required for proper operation.

The messaging service 1404 allows the user to send a text message to request a link to the required questionnaire. The user may be notified to access the questionnaire, e.g., by a notification push to the second user device 1006*b* or by instruction from the authorization system 1004 or the main entry system 1002 The user is instructed, e.g., by the QP, to provide his/her location by indicating the position ID in the body of the text. The messaging service 1404 parses the user's text for the location identification (ID). With the location ID the messaging service will then send this to the questionnaire application (see below) to determine which QP is associated with that location ID and obtain a URL to those questionnaires. The messaging service 1404 then sends the questionnaire(s) link(s) back to the user, preferably via SMS, with link(s) to the questionnaire(s) associated with that location (see FIG. 11).

The identity and authentication application (IAA) 1406 is configured to manage new identity and authentication inputs, and to ensure that new identity inputs (manual codes or unique identifiers of the first user device) are unique and never re-used. Additionally, The IAA 1406 also handles the secure storage of biometric data used for authentication purposes (see FIG. 11).

The hash generator 1408 (a.k.a. hashing function, cryptographic hashing algorithm) is configured to convert and securely store sensitive biometric data. The hash generator takes data of arbitrary size to data of a fixed size. This compresses the data to significantly reduce the amount of storage required to store data. It also reduces the amount of data that has to been shared over a network. A cryptographic hash algorithm for the hash generator provides additional security and privacy benefits, as the user's raw biometric data is never stored on the system. Although FIG. 10 shows the hash generator 1408 as a separate module, it may also be part of the IAA 1406.

The questionnaire application 1410 is configured for the creation, management, and hosting of questionnaires. Administrators can remotely access the application 1410 for managing the questionnaires and export submissions for data-keeping purposes. The user can access the questionnaires hosted by the questionnaire application 1410 via a URL or directly in the questionnaire viewer running on his/her second user device 1006*b*. The questionnaire as described above and provides a list of questions used to aid in health screening, regulatory, compliance, and/or corporate governance. The questionnaire is preferably saved on the database 1402. The questions from the questionnaire are requested to be filled out by the user. Each or some of the questions may be configured to be used as an additional authorization check for determining authorization. The user's response for question(s) used for authorization check must match a list of acceptable answers (provided by the administrator at time of questionnaire creation) to receive authorization to enter the secure space 114. Otherwise, authorization is denied. The questionnaire may be delivered to the user in different ways. The system 1000 may disable/enable functionalities based on the deliver method selection based on the system configuration for the particular user. The delivery of the questionnaire may be through geofencing as discussed above. When the second user device 1006*b* is within a pre-defined perimeter, preferably within about 50 m the secure space 114, any required questionnaire(s) is automatically sent to the second user device 1006*b*. The location is determined by the OS location services running on the second user device 1006*b*. The location may also be determined by WiFi, Bluetooth, GPS, or other triangulation methods. The delivery of the questionnaire may also be through the QP 1314 or the remote questionnaire pointer (RQP) 1102 (as describe below). The QP 1314 or RQP 1102 are devices that provide a questionnaire URL to the user. Depending on the capabilities of the device that is providing the URL, there are two types: passive QP and broadcast QP. Passive QPs require the user to manually perform an action to get a link to the URL. For example, the user can scan a QR code, request a URL via SMS, or type in a URL displayed by the device. Broadcast QPs use devices equipped with radios which broadcast the URL. The questionnaire viewer 1216 running on the second user device 1006*b* receives the radio broadcast when it is within radio range, and notifies the user that a questionnaire must be completed to access the secure space 114. The radio broadcast may be implemented with WiFi, Bluetooth, or NFC. The user's responses expire on after a predetermined amount of time or when the questions are no longer in use, whichever comes first. The predetermined amount of time depends on the particular question and may be from about 1 day to about several years. For example, for a COVID 19 questionnaire, the expiration may be daily. On the other hand, for an NDA, the expiration may be determined by the language of the NDA. A list of devices used as QPs (RQPs 1102 and QPs 1314) associated with a particular questionnaire are also saved in the database 1402. The URL provided to the user preferably contains an identifier to allow the authorization system 1004 to know which device is used to obtain the URL. If the device is not associated with a questionnaire, as set by the system configuration, the user is not presented with a questionnaire. A list of users who have completed the questionnaire is also saved on the database 1402.

The authorization application 1412 is used to configure the authorization checks required for a particular user or user group. The configuration may be dome by the system administrators. The authorization application 1412 creates and maintains the user data object saved on the database 1402. The authorization application 1412 uses the user data object to grant access to the user. When the user requests access, the main entry system 1002 only grants access if the authorization application 1412 determines all of the user's authorization checks have been met. The user data object is unique to each particular user and used by the authorization system 1004 to determine authorization access, and inform the system how the user can provide authentication/identity inputs to the system. The particular information contained in the user data object is explained below. The authorization system 1004 also maintains a list of the authorization checks required for each particular user to gain access to the secure space 114. For all users, however, identification is always required to gain access. Two other authorization checks may also be required of the user to gain access: an authentication input (to authenticate the user entering the identity input) and/or questionnaire responses. The additional authentication may be facial or voice recognition, for example. If additional authentication is required, the hashed value of the raw authentication input (facial or vocal), if that input method is selected, is generated and saved in the database 1402. The authorization application 1412 may also be used to define input methods for each particular user. Depending on the particular user, the authentication and identity input methods may differ. For example, a CEO may be required to have a more secure method of authenticating themselves when compared to a janitor. Depending on the user, no authentication may be necessary or one or more input methods may be required (depending on the level of security required to enter the secure space 114).

One authentication input method is approval from the second user device. Here, when the user uses his first user device 1006a, e.g., at the barrier 1110 or his assigned code (as described below), the user is presented with a notification that their identity is being used at the particular barrier 1110. This notification is delivered via the questionnaire viewer 1216 running on the second user device 1006b. The user must then approve that they are the one using the first user device 1006. If the user does not approve this within a specific time window, for example within 60 seconds, the process must be restarted.

Another authentication input method uses an alphanumeric value comparison method. Here, when the user uses the first user device 1006a, e.g., at the barrier 1110 or the assigned code (as described below), the main entry system 1002 displays an alphanumeric value to the user, e.g., on the digital display of the QP 1314 located proximate to the barrier 1110. The user must enter this value into the questionnaire viewer 1216, which is then sent to the authorization application 1412 for comparison. If the user-provided input matches the value displayed to him/her, this authorization check is complete.

A further authentication input method uses proximity of the second user device to the radio module on the main entry system 1002. Here, when the user uses the first user device 1006a or the assigned code (as described below), e.g., at the barrier 1110, the radio module on the QP proximate to the barrier 1110 is configured to broadcast. If the second user device 1006b is within proximity of the radio, the questionnaire viewer 1216 running on the second user device 1006b communicates to the authorization system 1004 that this user is in close proximity to the entry system 1002, which may be used as an authentication input.

Yet another input method uses biometric data, such as facial recognition and/or voice recognition. Here, when the user uses the first user device 1006a or the assigned code (as described below), e.g., at the barrier 1110, the main entry system 1002 requests a facial and/or voice recording from the user, preferably via the questionnaire viewer 1216 running on the second user device 1006b. The questionnaire viewer 1216 may capture the user's facial image by the camera 1208 on the second user device 1006b. Alternatively, the authentication input on the main entry system 1002 can be used for image capture. The camera may be mounted near the barrier 1110. For voice recognition, the user's voice may be recorded by the questionnaire viewer 1216 using the microphone 1210 on the second user device 1006b. Alternatively, the authentication input device 1312 on the main entry system 1002 may be used for voice capture. The authentication input device 1312 may be equipped with a microphone that may be mounted near the barrier 1110.

Each user may use the first user device 1006a as the first factor for identity input. The first user device is assigned a unique identifier which is transmitted to the main entry system 1002 when the user uses the first user device 1006a to request access. Alternatively, the user may be assigned a code to be entered into the main entry system 1002 to request access. The assigned code may be entered, e.g., on a keypad provided by the identity input device 1310 on the main entry system 1002. The unique identifier is the user's unique value that is used for identity input verification. Depending on how the user's input methods are configured, it is either the unique identifier provided on the first user device 1006a or the manual code that the user enters.

The administration device 1104 is used by administrators for configuring and monitoring the main entry system 1002 and/or the authorization system 1004. The administration device 1104 may be a computer, smart phone, or tablet connected wirelessly or by wire to the network 1100 via a network interface 1500, which is similar to the previously described network interfaces 1300, 1400. The administrative device 1104 also preferably includes one or more of the following modules: a user interface 1502, a database 1504, and a notification hander 1506. The user interface 1502 is used by the administrator to access and configure the main entry system 1002 or the authorization system 1004. The database 1504 is used to store system configurations and load user data. The notification hander 1506 is used to receive notifications of abnormal events observed by the authorization system. An example of an event would be when a user has failed to the authorization checks multiple times.

The system 1000 may also include a remote questionnaire pointer (RQP) 1102 which is preferably a permanently fixed device, such as a sign, that may be connected to the network 1100 (hence the broken line connecting the RQP 1102 with the network 1100). Examples of the QP 1102 may be a parking sign, a sign along a walkway, or a sign at the barrier 1110 that provides instructions to the user seeking to enter a building/parking lot. The RQP 1102 preferably provides a URL link to a questionnaire/survey that visitors of a building must fill out before entry. The sign may be an electronic sign that is connected to the network 1100. The QP 1102 provides the URL link by giving a static QR Code or phone number for receiving the URL via text. More advanced implementations may broadcast the URL via a radio embedded into the device. In the latter, the sign may be equipped with a solar panel to power the radio. The RQP 1102 may be controlled by the access controller similarly to the one QP 1314 described above for questionnaire delivery.

Figure 12:
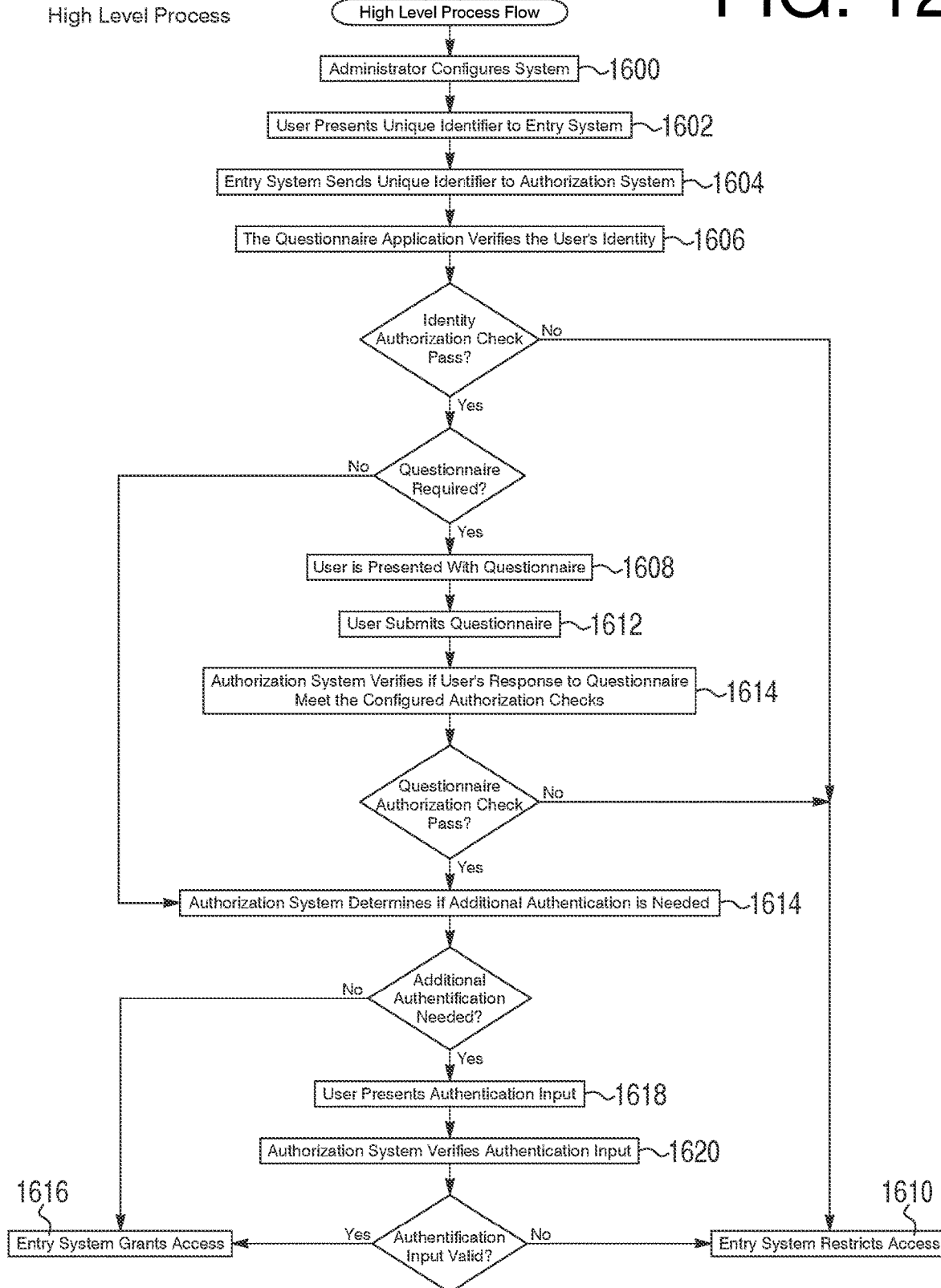
FIG. 12 is a flow chart showing operation of the exemplary entry system.

FIG. 12 is a flow chart showing a high-level operation of the exemplary entry system 1000. Once the system is configured by the administrator (box 1600), the system 1000 may be operated to control access to a secure space 114. Once the user presents his/her unique identifier (identity input) to the main entry system 1002 (box 1602), e.g., by scanning his/her first user device 1006a or entering his/her code into the main entry system 1002, the main entry system 1002 sends the unique identifier to the authorization system 1004 (box 1604) for verification by the questionnaire application 1410 (box 1606). If the identity check fails, entry is denied (box 1610). If the identity check passes, the questionnaire is sent to the user if one is required (box 1608). Once the user responds to the questionnaire (box 1612), the response is sent to the authorization system 1004 for authorization. If the response fails, access is denied. If the response passes, the authorization system 1004 determines whether additional authentication is needed (box 1614). If not, access is granted (box 1616). If additional authorization is needed, the user is presented with additional authentication input (box 1618), e.g., facial and/or voice recognition. Once the user enters the additional authentication input, it is verified by the authorization system 1004 (box 1620). If verification fails, access is denied (box 1610); if verification passes, access is granted (box 1616).

Figure 13:
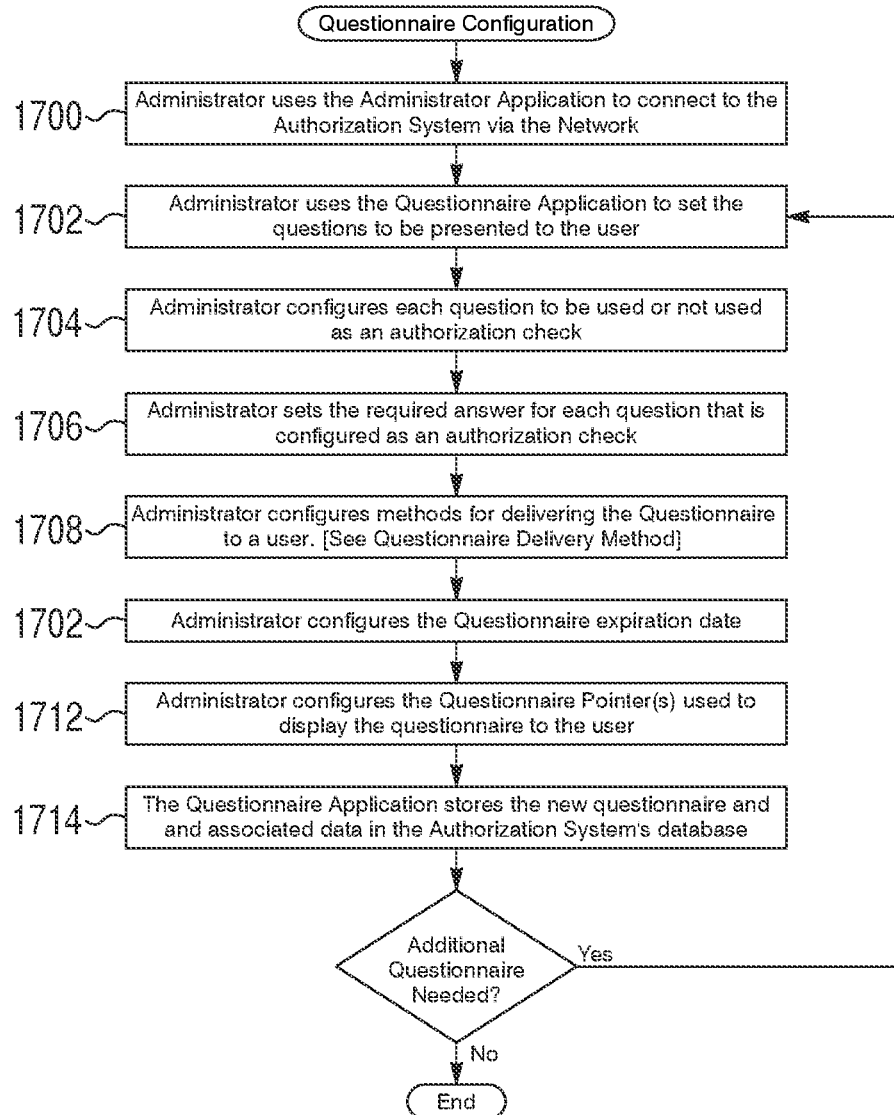
FIG. 13 is a flow chart showing the questionnaire configuration process.
Figure 14:
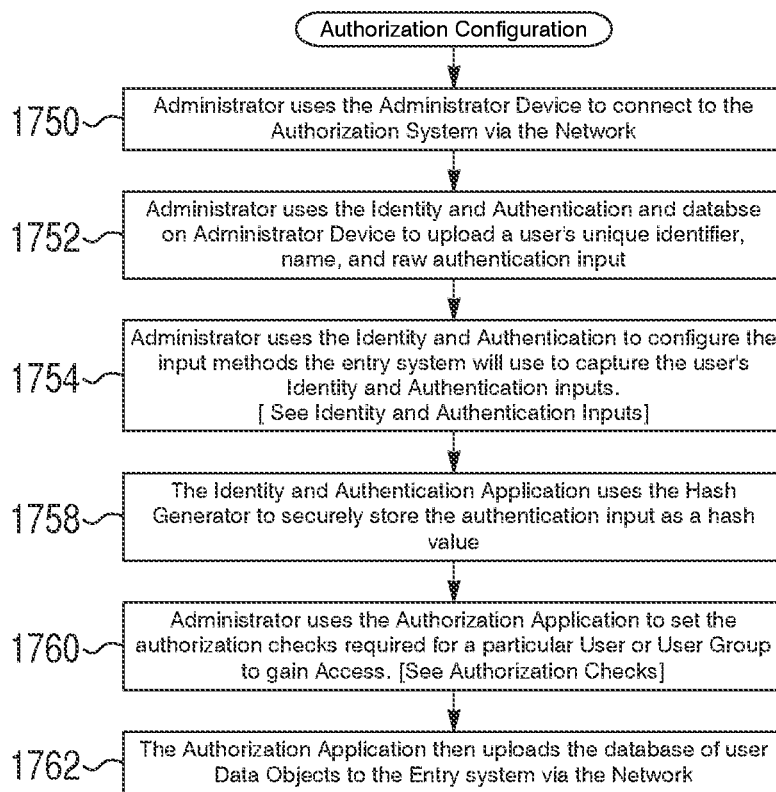
FIG. 14 is a flow chart showing the authorization configuration process.

FIGS. 13 and 14 shows the questionnaire configuration and the authorization configuration, respectively. Referring to FIG. 13, the administrator uses the administrator device 1104 to connect to the authorization system 1004 and the main entry system 1002 via the network 1100 (box 1700). Once connected to the authorization system 1004, the administrator uses the questionnaire application 1410 to set the questions to be presented to the user (box 1702). For each question, the administrator configures it as an authorization check or not (box 1704). The administrator then sets the required answer(s) for each question that is configured as an authorization check (box 1706). The administrator then configures the methods for delivering the questionnaire to the user (box 1708), e.g., by geofencing, SMS, passive pointer, and/or broadcast pointer, and the questionnaire expiration date (box 1710). The administrator then configures the QP 1314 used to display the questionnaire to the user (box 1712). The configuration process may simply a drop down menu with a list of RQPs and main entry systems for the administrator to select and configure. The questionnaire application 1410 then stores the questionnaire and associated configuration data in the database 1402 on the authorization system 1004 (box 1714). The process is then repeated until all required questionnaires are configured.

Referring to FIG. 14, the administrator uses the administrator device 1104 to connect to the authorization system 1004 via the network 1100 (box 1750). The administrator then uses the identity and authentication application 1406 on the authorization system 1004 and the database 1504 on the administrator device 1104 to upload each user's unique identifier, name, and raw authentication input to the database 1402 of the authentication system 1004 (box 1752). The administrator then uses the identity and authentication application 1406 to configure the input methods for entry system 1002 used to captures the user's identity and authentication input (box 1754). The identity and authentication application 1406 then uses the generator 1408 to securely store the authentication input as a hash value (box 1756). The administrator then uses the authorization application 1412 to set the authorization checks required for each particular user or user group to gain access (box 1758). The authorization application 1412 next stores a user data object for each user in the database 1402 of the authentication system 1004 (box 1760) which includes the user's unique identifier, name, authentication input hash, input methods, and associated authorization checks. The authorization application 1412 may then upload the database of user data objects to the main entry system 1002 via the network 1100 [. Uploading to the user data objects to the main entry system 1002, however, is an alternative approach. Ordinarily, the user data objects are stored only in the authentication system 1004.

Figure 15:
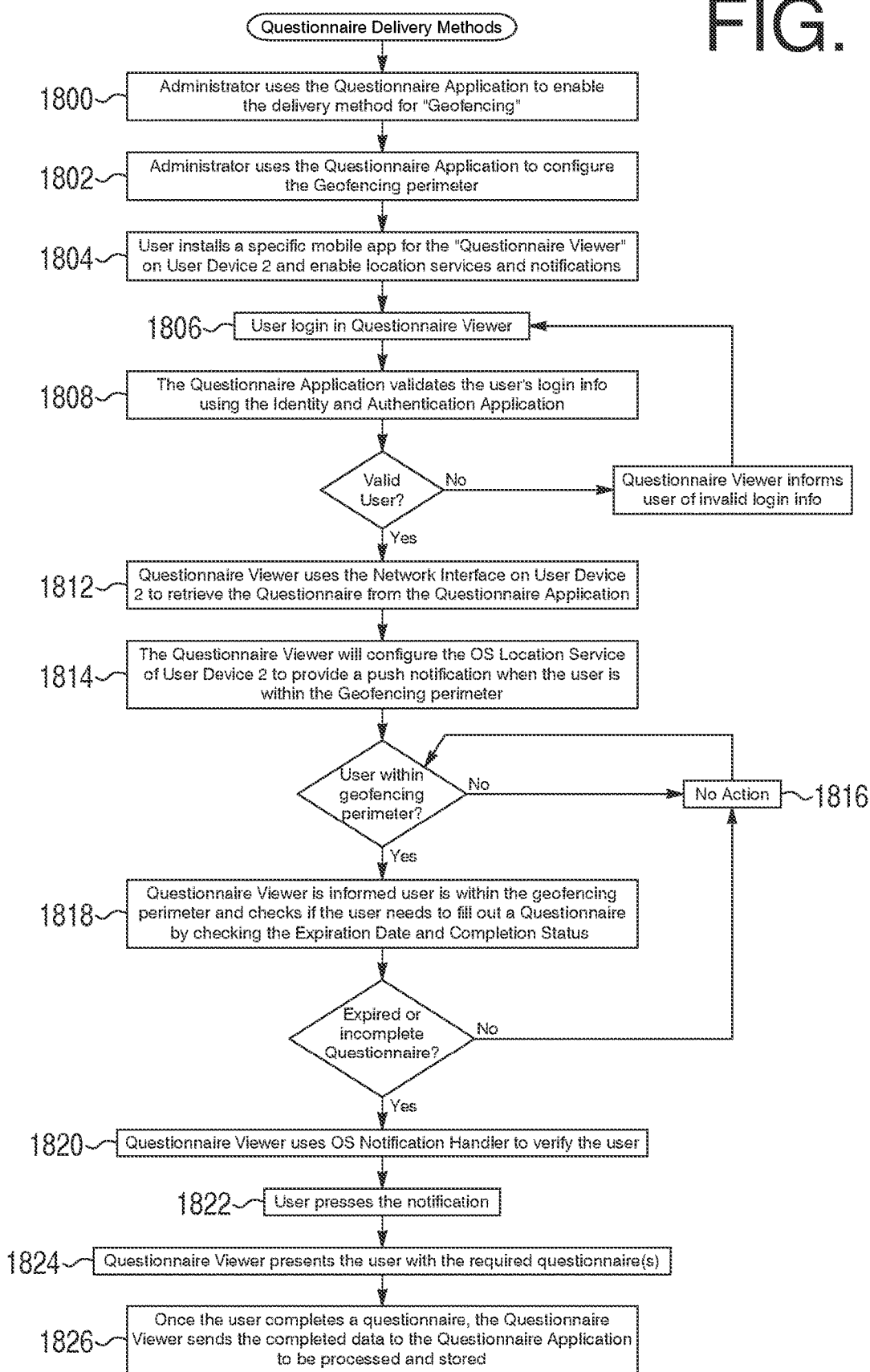
FIG. 15 is a flow chart showing a method for delivery of the questionnaire using geofencing.

FIGS. 15-18 show methods for the exemplary system 1000 to deliver the questionnaire to the user, including via geofencing, passive pointer, radio broadcast pointer, and SMS, respectively. Referring to FIG. 15, which is a flow chart showing a method for geofencing delivery of the questionnaire, the administrator enables the geofencing delivery method (box 1800) and the geofencing perimeter (box 1802) using the questionnaire application 1410. To use geofencing delivery, the user must enable the questionnaire viewer 1216, the location service 1206, and notifications 1210 on the second user device 1006b (box 1804). The user must also login to the questionnaire viewer 1216 (box 1806) and have the login information validated by the questionnaire application 1410 in the authorization system 1004 (box 1808). Once logged in, the questionnaire viewer 1216 uses the network interface 1200 on the second user device 1006b to retrieve the questionnaire from the questionnaire application 1410 (box 1812). The questionnaire viewer 1216 configures the OS location service 1206 on the second user device 1006b to provide a push notification when the second user device 1006b is within the geofencing perimeter (box 1814). This configuration is preferably accomplished at the time the questionnaire viewer 1216 is installed on the second user device. Once within the geofencing perimeter, the questionnaire viewer 1216 informs the user that he/she is within the perimeter and checks to determine whether the user needs to fill out a questionnaire by checking the expiration date and completion status of the questionnaire (box 1818). If there is no expired or incomplete questionnaire, no action is taken (box 1816). Otherwise, the questionnaire viewer 1216 uses the OS notification handler to notify the user that a questionnaire is required to be successfully completed (box 1820). Once, the user presses the notification (box 1822), the questionnaire viewer 1216 presents the user with the required questionnaire(s) (box 1824). Once the user completely responds to the questionnaire, the questionnaire viewer 1216 sends the completed response to the questionnaire application 1410 to be processed and stored (box 1826).

Figure 16A:
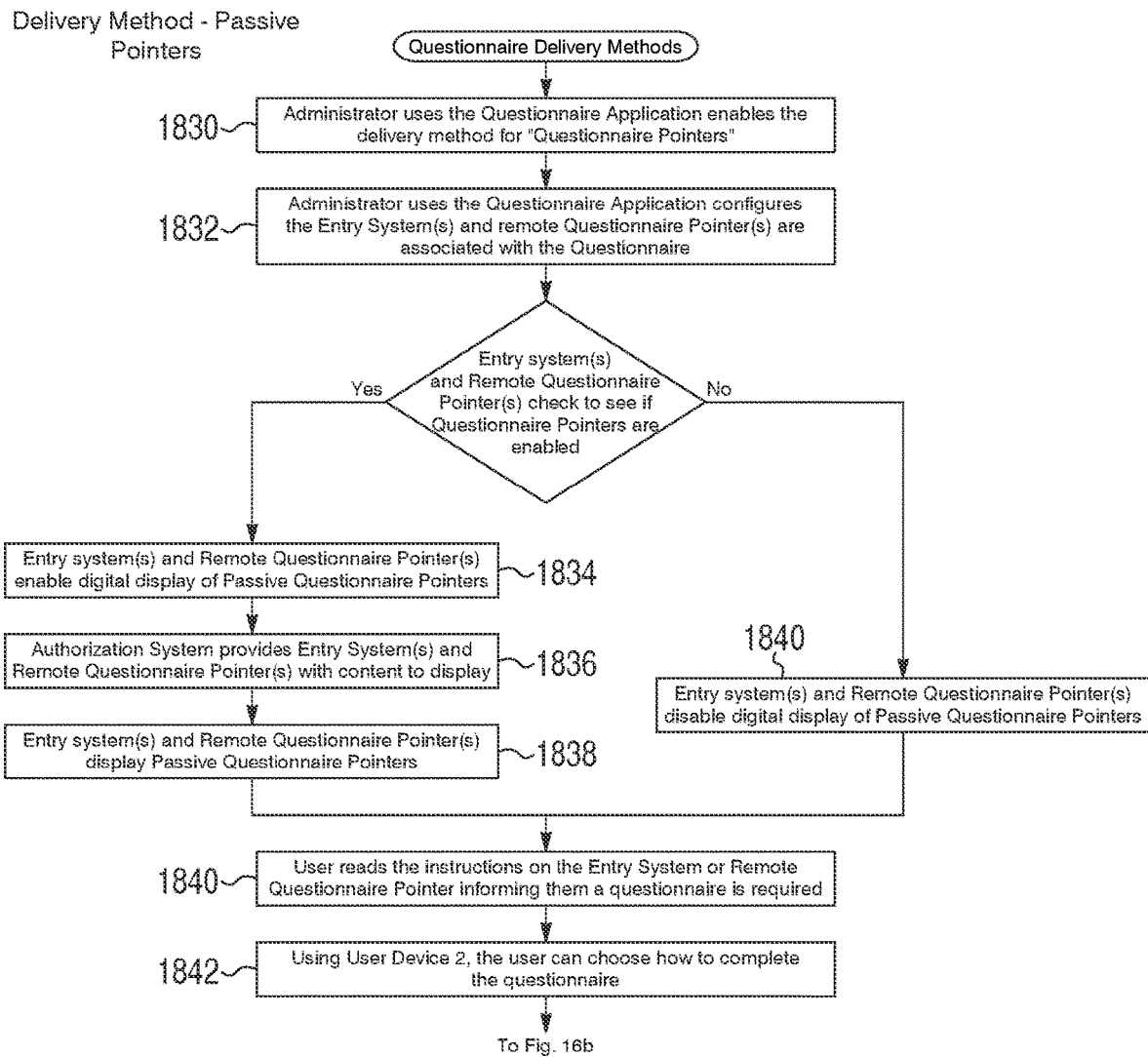
FIGS. 16a and 16b are flow charts showing a method for delivery of the questionnaire using passive pointers (FIG. 16b is a continuation of FIG. 16a)
Figure 16B:
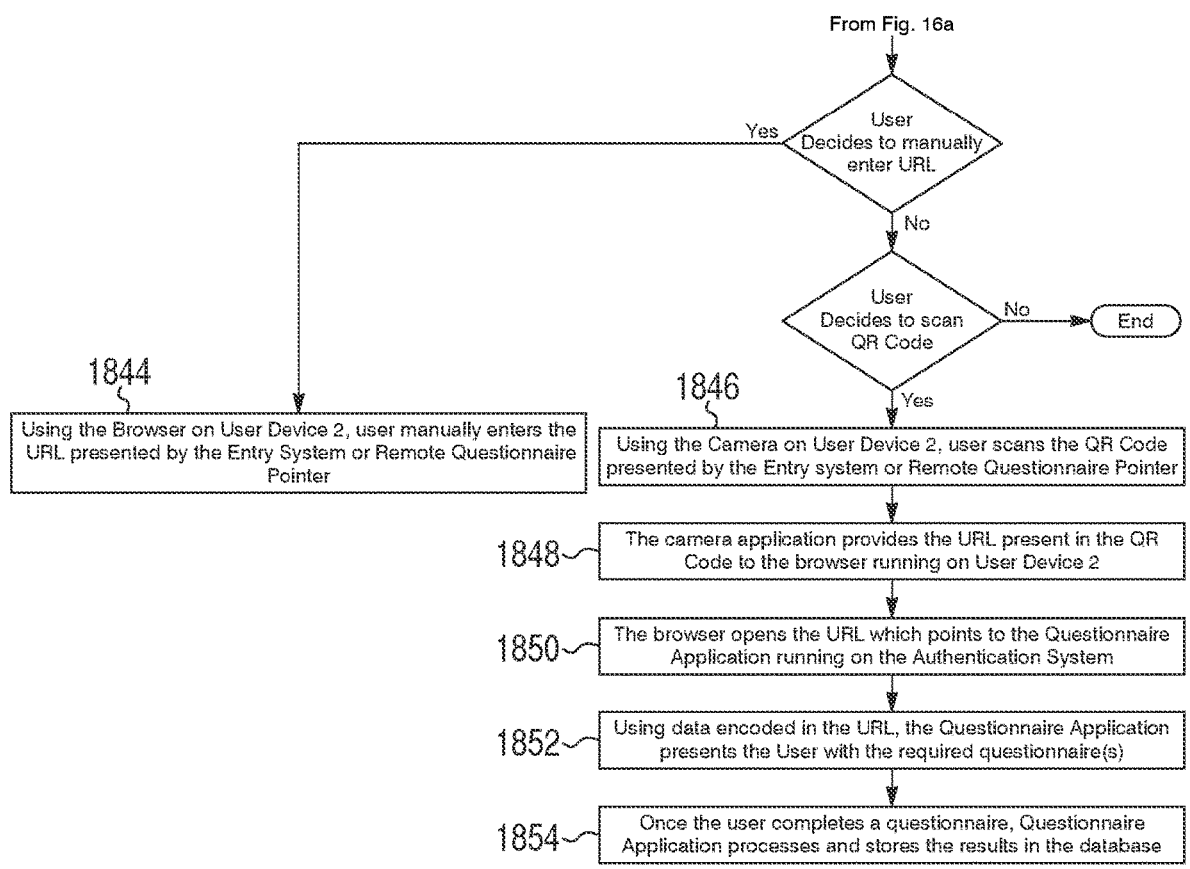

Referring to FIGS. 16a and 16b, which show a method for delivery of the questionnaire by passive pointer, the administrator, using the questionnaire application 1410, enables the passive delivery method (box 1830) and configures the particular main entry system 1002 and RQP 1102 to be associated with the questionnaire (box 1832). Once enabled and configured, the main entry system 1002 and the RQP 1102 enables digital displays of the passive pointer (box 1834). The authorization system 1004 then provides the main entry system 1002 and the RQP 1102 with content to display on the digital display (box 1836). The main entry system 1002 and the RQP 1102 display the passive questionnaire pointer on their digital display (box 1838). The user then reads the content shown on the digital display of the main entry system 1002 or the RQP 1102 informing him/her a questionnaire is required (box 1840). Using the second user device 1006b, the user can choose to complete the questionnaire (box 1842) by manually entering the URL or by scanning the QR code on the digital display. To manually enter the URL, the user may use the browser 1212 on the second user device 1006b to enter the URL presented on the main entry system 1002 or the RQP 1102 (box 1844). To scan the QR code, the user uses the camera 1208 on the second user device 1006b to scan the QR code presented by the main entry system 1002 or the RQP 1102 (box 1846) which provides the URL present in the QR code to the browser 1212 on the second user device 1006b (box 1848). In either case, the browser 1212 opens the URL which is lead to the questionnaire application 1410 running on the authorization system 1004 (box 1850). Using the data encoded in the URL, the questionnaire application 1410 presents the user with the require questionnaire(s) on the browser 1212 on the second user device 1006b (box 1852). Once the user responds to the questionnaire(s), the questionnaire application 1410 processes and stores the results in the database 1402 (box 1854).

Figure 17:
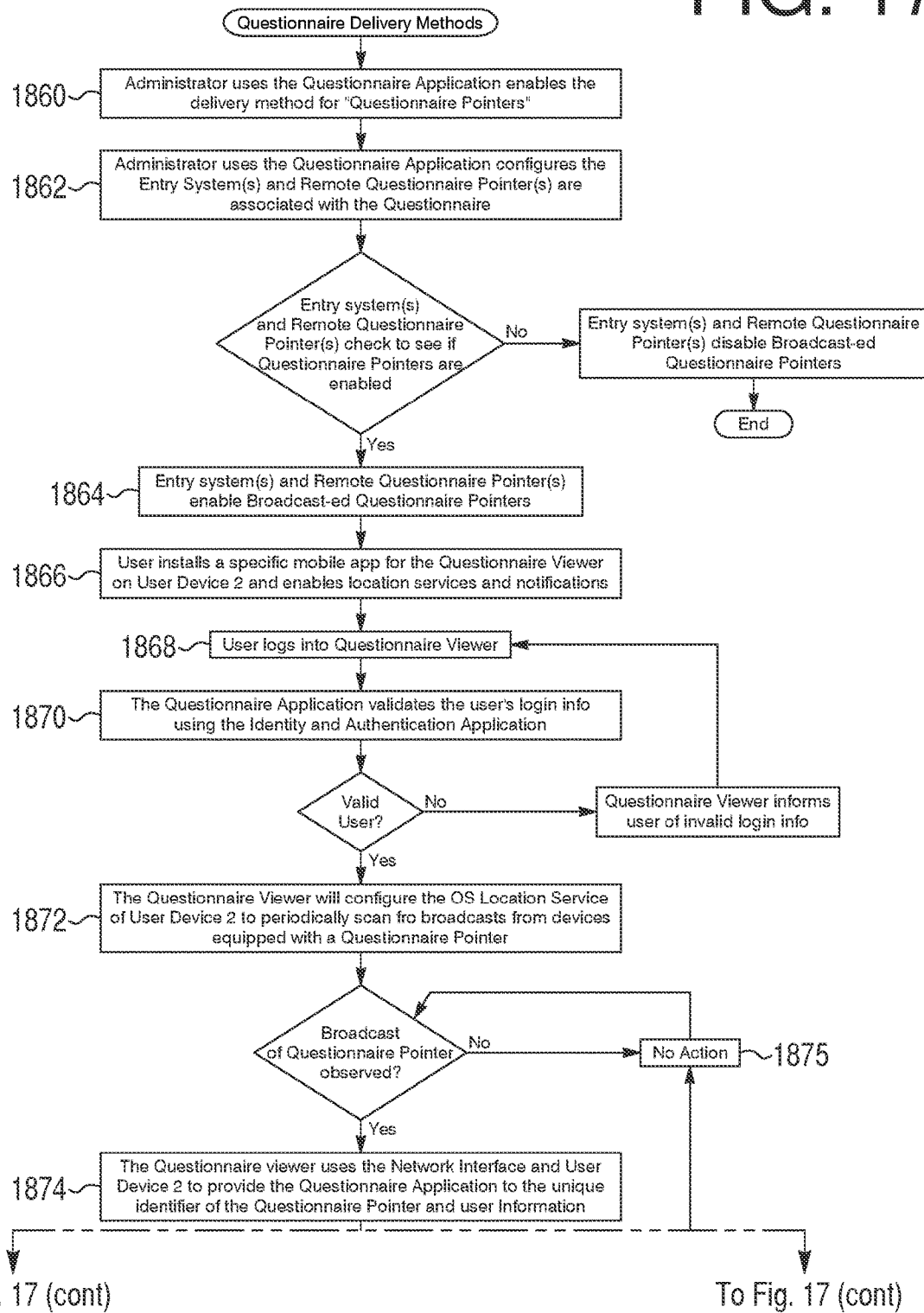
FIG. 17 is a flow chart showing a method for delivery of the questionnaire using broadcast pointers.
Figure 17:
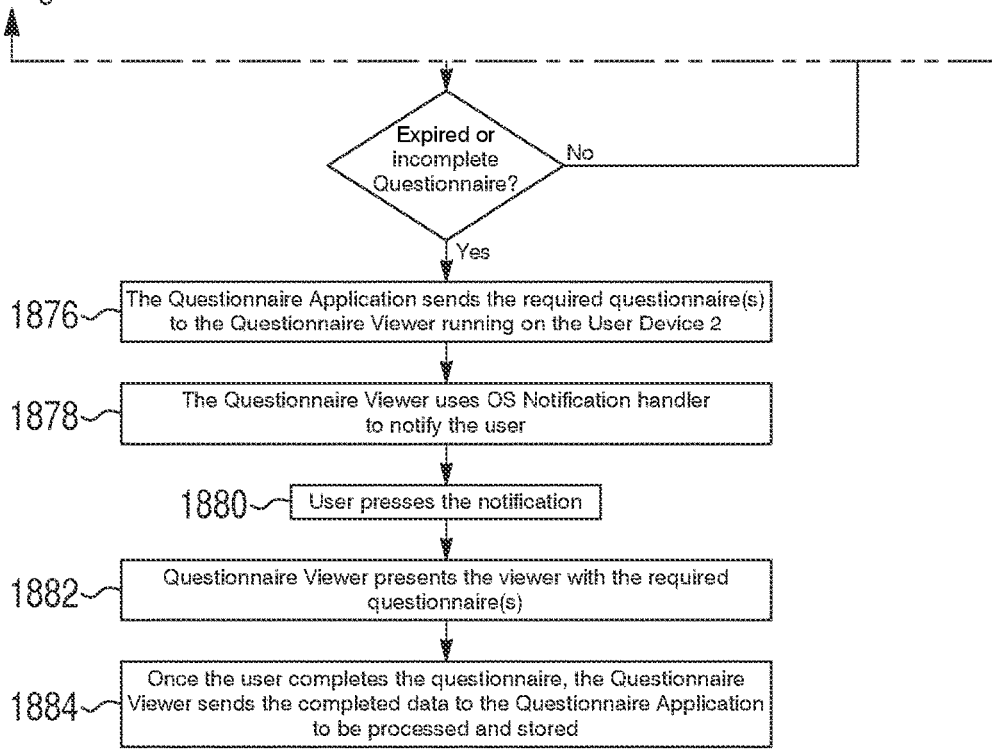

Referring to FIG. 17, which is a flow chart showing a method for delivery of the questionnaire by broadcast pointers, the administrator, using the questionnaire application 1410, enables the broadcast delivery method (box 1860) and configures the particular main entry system 1002 and RQP 1102 to be associated with the questionnaire (box 1862). This method uses radio broadcast of the URL as discussed above. Once enabled and configured, the main entry system 1002 and the RQP 1102 enable radio broadcasting of the questionnaire pointer (box 1864). To use broadcast delivery, the user must enable the questionnaire viewer 1216, the location service 1206, and notifications 1210 on the second user device 1006*b* (box 1866). Preferably, the questionnaire viewer 1216 is logged on and is running in the background of the second user device 1006*b*. Alternatively, the user may be reminded by the RQP to log in to the questionnaire viewer 1216 on the way to the secure space 114. The user must also login to the questionnaire viewer 1216 (box 1868) and have the login information validated by the questionnaire application 1410 in the authorization system 1004 (box 1870). Once logged in, the questionnaire viewer 1216 configures the OS location service 1206 on the second user device 1006*b* to periodically scan for the radio broadcast from the main entry system 1002 or the RQP 1102 (box 1872). When the broadcast is detected, the questionnaire viewer 1216 uses the network interface 1200 on the second user device 1006*b* to provide the questionnaire application 1410 on the authorization system 1004 with the unique identifier of the questionnaire pointer and user information (box 1874). If there is no expired or incomplete questionnaire, no action is taken (box 1875). Otherwise, the questionnaire application 1410 sends the required questionnaire(s) to the question questionnaire viewer 1216 running on the second user device 1006*b* (box 1876). Once the questionnaire(s) is received, the questionnaire viewer 1216 uses the OS notification handler 1204 to notify the user (box 1878). Once, the user presses the notification (box 1880), the questionnaire viewer 1216 presents the user with the required questionnaire(s) (box 1882). Once the user completely responds to the questionnaire, the questionnaire viewer 1216 sends the completed response to the questionnaire application 1410 to be processed and stored (box 1884).

Figure 18A:
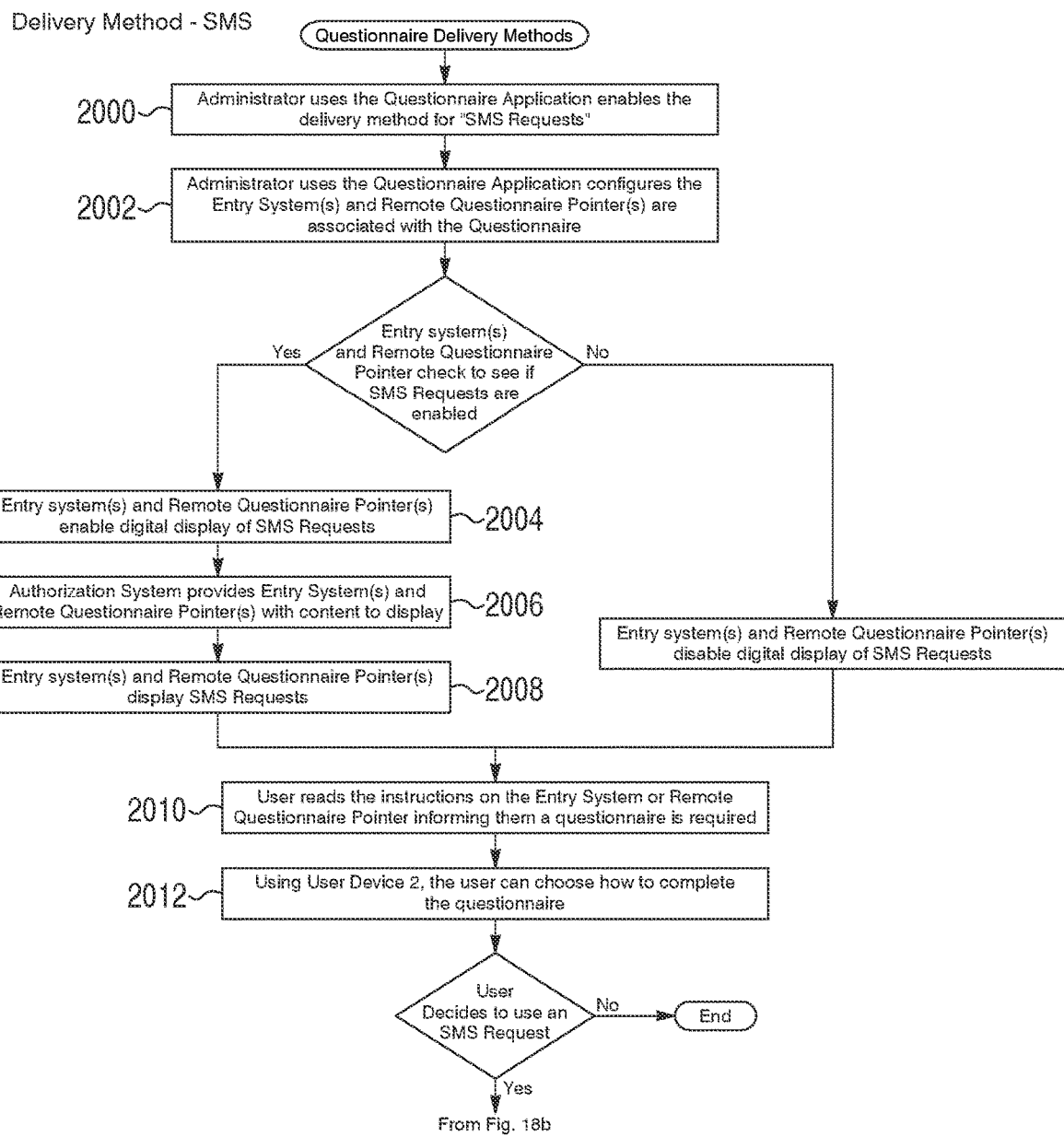
FIGS. 18a and 18b are a flow charts showing a method for delivery of the questionnaire using text messaging (FIG. 18b is a continuation of FIG. 18a)
Figure 18B:
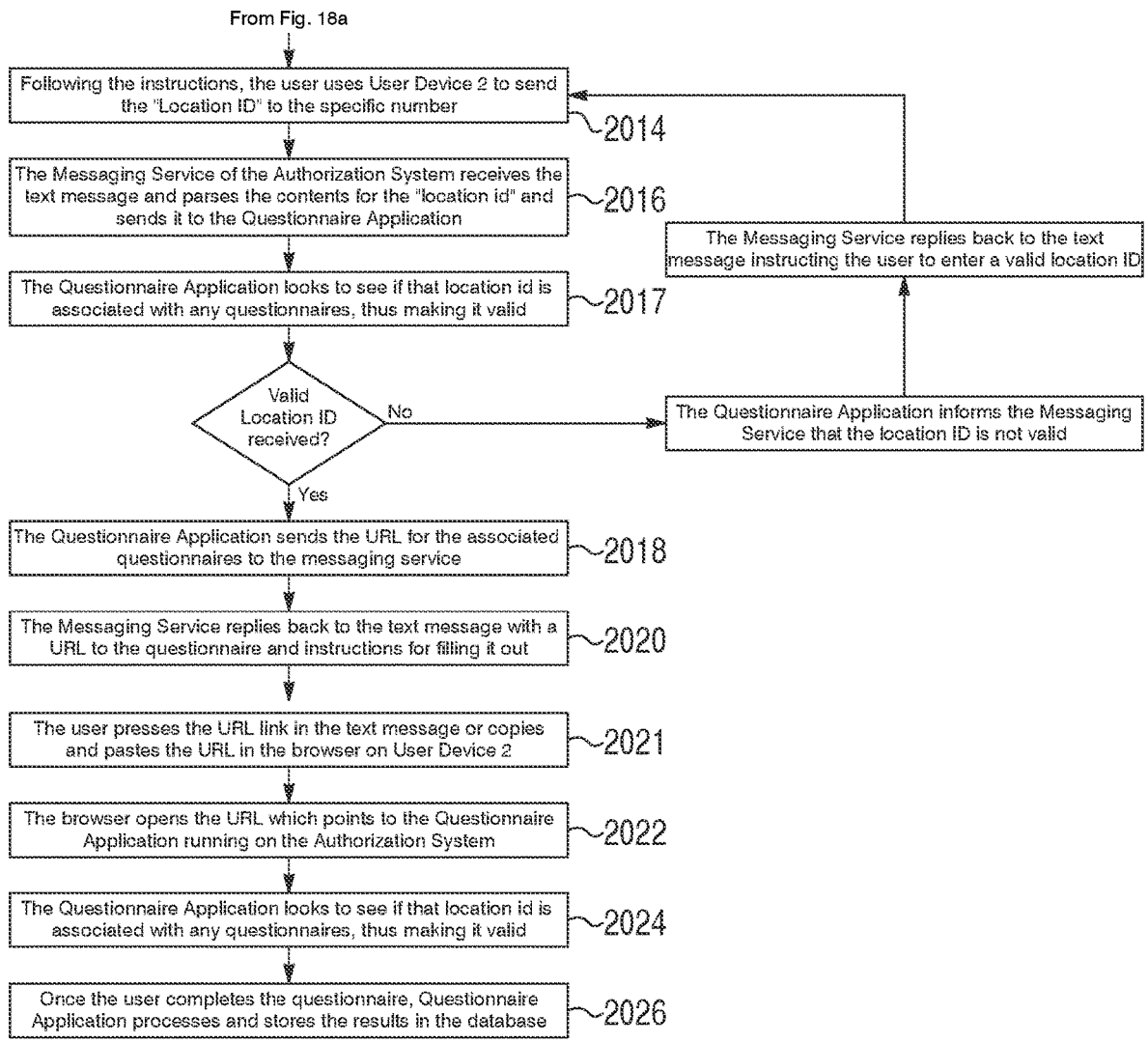

Referring to FIGS. 18*a* and 18*b*, which are a flow charts showing a method for delivery of the questionnaire by text messaging (a.k.a. SMS). The administrator, using the questionnaire application 1410, enables the SMS delivery method (box 2000) and configures the particular main entry system 1002 and RQP 1102 to be associated with the questionnaire (box 2002). Once enabled and configured, the QP 1314 of the main entry system 1002 and/or the RQP 1102 enable their digital displays for the SMS request (box 2004). The authorization system 1004 then provides the RQP 1102 or QP 1314 with content to display on the digital display (box 2006). The RQP 1102 or QP 1314 then display the SMS request on their digital displays (box 2008). The user then reads the content shown on the digital display of the QP of the or the RQP 1102 informing him/her that a questionnaire is required (box 2010). Using the second user device 1006*b*, the user can choose to complete the questionnaire (box 2012) by requesting the questionnaire by following the instructions on the QP 1314 or the RQP 1102 (box 2012) and texting the location ID of the RQP or QP to the number specified by the instructions (box 2014). The messaging service 1404 of the authorization system 1004 receives the text message and parses its contents for the location ID of RQP or QP and sends the location ID to the questionnaire application 1410 (box 2016). The questionnaire application 1410 determines, by looking to the database 1402, whether that location ID is valid and whether any questionnaire(s) is associated with that location (box 2017). If the user provided location ID matches and one or more questionaries are required, then the location ID is valid, and the messaging service 1404 replies back to the text message with an URL to access the questionnaire and instructions for filling out the questionnaire (boxes 2018 and 2020). The user can press on the URL link in the text message or copy and paste the URL in the browser 1212 on the second user device 1006*b* (box 2021) to access the questionnaire. The browser 1212 then opens the URL which is lead to the questionnaire application 1410 running on the authorization system 1004 (box 2022). Using the data encoded in the URL, the questionnaire application 1410 presents the user with the require questionnaire(s) on the browser 1212 of the second user device 1006*b* (box 2024). Once the user responds to the questionnaire(s), the questionnaire application 1410 processes and stores the results in the database 1402 (box 2026).

Figure 19:
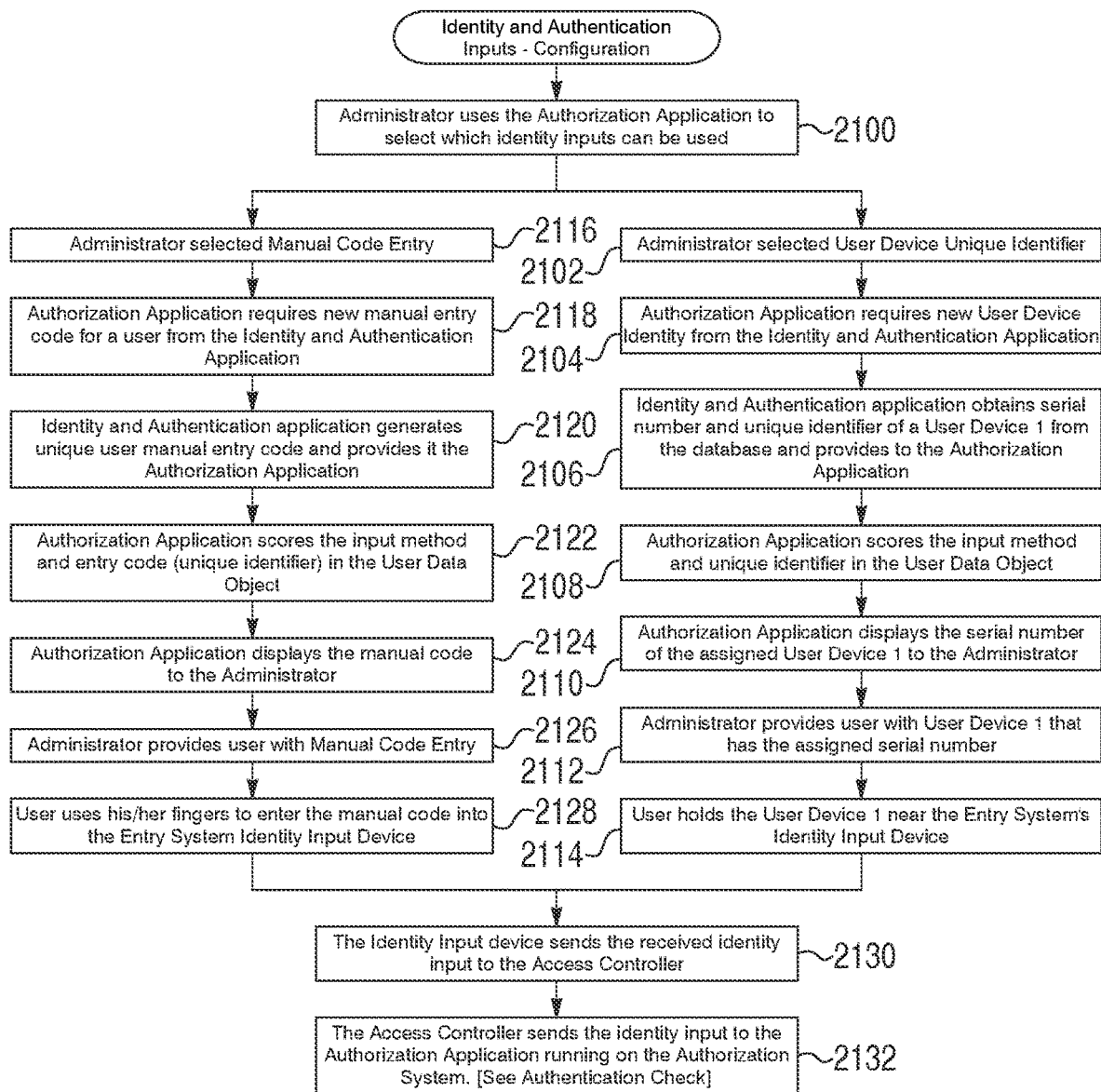
FIG. 19 is a flow chart showing the identity input configuration process the user must follow to gain access to the secure space

FIG. 19 is a flow chart showing the identity input process the user must follow to gain access to the secure space 114. The identity input process is generally discussed above and shown in box 1602 of FIG. 12. The administrator uses the authorization application 1412 (accessed via the administrator device 1104) to select the kind of identity input to be used by the user (box 2100). Two kinds of identity inputs may be selected: manual code entry (box 2116) or first user device (box 2102). The administrator selects one or both input methods for an individual user. The administrator may also select no identity for a particular user, in which case, no identity input is needed when that user requests entry to the secure space 114 (other requirements, such as questionnaire and/or facial or voice recognition may still be applicable to that user to gain entry).

For manual code input, the authorization application 1412 requests a new manual entry code for the user from the identity and authentication application 1406 (box 2118), causing the identity and authentication application 1406 to generate a unique manual entry code (unique identifier) and to provide it to the authorization application 1412 (box 2120). The authorization application 1412 stores the input method and entry code (unique identifier) in the user data object for that particular user (box 2122), preferably in the database 1402 of the authorization system 1004. The authorization application 1412 then displays the manual entry code to the administrator (box 2124) who then provides it to the user (box 2126). The user then manually enters the code into the identity input device 1310 of main entry system 1002 (box 2126).

For using the first user device 1006*a*, the authorization application 1412 requests a new first user device 1006*a* unique identifier for the user from the identity and authentication application 1406 (box 2104), causing the identity and authentication application 1406 to obtain the serial number and unique identifier of the first user device 1006*a* from the database 1402 and to provide them to the authorization application 1412 (box 2106). The authorization application 1412 stores the input method and unique identifier in the user data object for that particular user (box 2108). The authorization application 1412 then displays the serial number of the first user device 1006*a* to the administrator (box 2110) who then provides the first user device to the user for use when requesting entry to the secure space 114 (box 2112). To initiate entry request, the user scans the first user device 1006*a* at the identity input device 1310 of main entry system 1002 (box 2114).

In either event (manual code entry or use of the first user device 1006*a*), the identity input device 1310 sends the received identity input to the access controller 1306 on the main entry system (box 2130). The access controller 1306 then forwards the identity input to the authorization application 1412 running on the authorization system 1004 to initiate authentication check (box 2132).

Once the identity input is completed, the system 1000, if configured to do so for the particular user, conducts an authentication check to verify that the user who presented the identity input is allowed to gain entry to the secure space 114 (authentication). FIGS. 20-23 show different authentication checks that may be selected by the administrator for a particular user. The administrator may select approval from 1) the second user device 1006b (FIG. 20); 2) alphanumeric input (FIG. 21); 3) proximity to the main entry system (FIG. 22); and 4) biometric data (FIG. 23).

Figure 20:
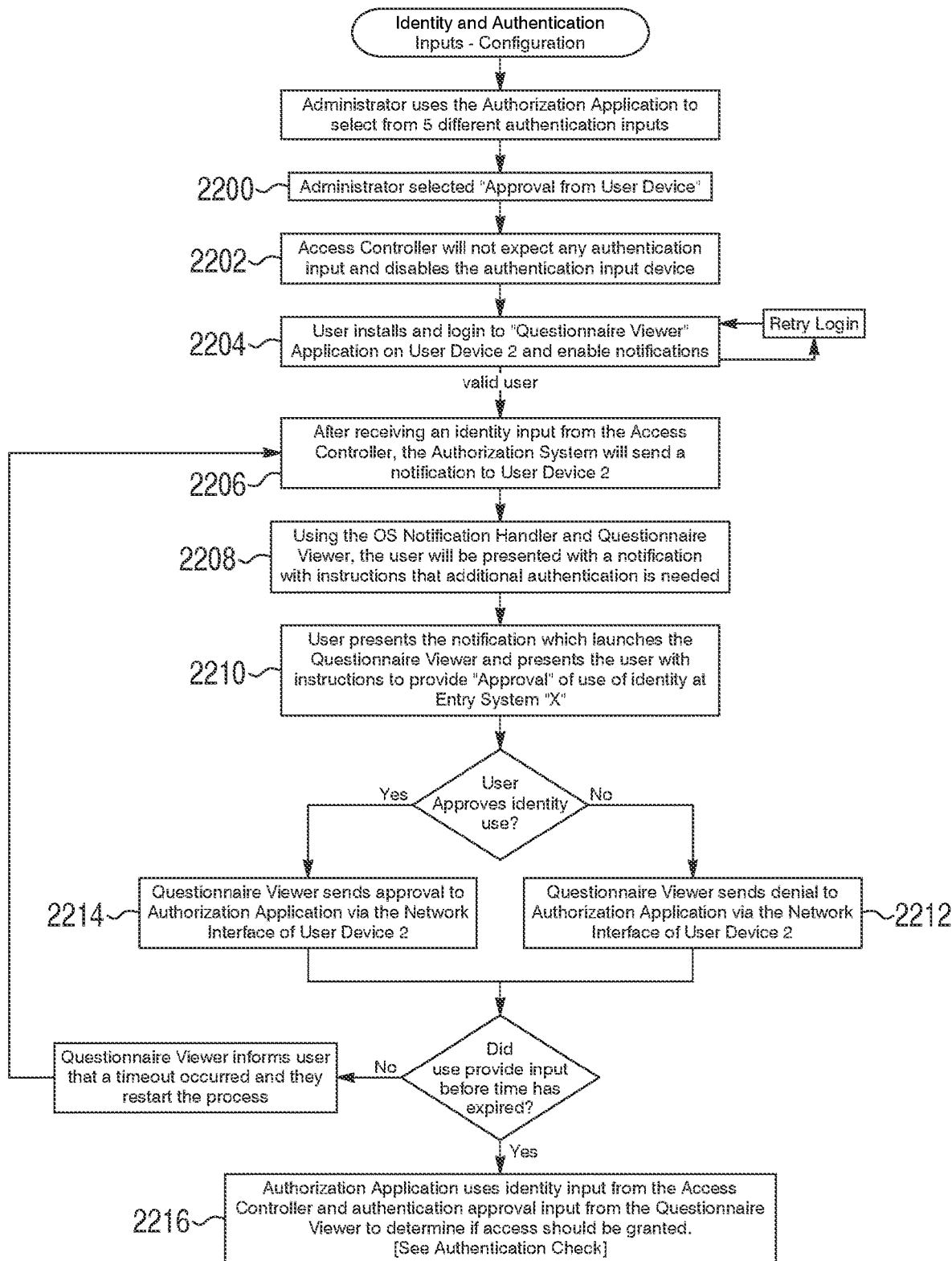
FIG. 20 is a flow chart showing the authentication input using the second user device.

Referring to FIG. 20, which is a flow chart showing the authentication input using the second user device 1006b (box 2200), the access controller 1306 disables the authentication input device 1312 on the main entry system 1002 (box 2202). To initiate authentication, the user logs into the questionnaire viewer 1216 and enables notifications on the second user device 1006b (box 2104). Preferably, the questionnaire viewer 1216 is logged on and is running in the background of the second user device 1006b. Alternatively, the user may be reminded by the RQP to log in to the questionnaire viewer 1216 on the way to the secure space 114. After receiving the identity input from the access controller 1306 (box 2132 in FIG. 19), the authorization system 1004 sends a notification to the second user device 1006b (box 2206). Through the OS notification handler 1204 and the questionnaire viewer 1216 on the second user device 1006b, the user is presented with a notification and instructions that additional authentication is needed (box 2208). When the user presses the notification, the questionnaire viewer 1216 is launched to present the user with instruction to provide approval for use of identity at the particular main entry system 1002 (box 2010). The user either approves (box 2014) the use or not (box 2012) which is sent to the authorization application 1412 on the authorization system 1004. In either case, the authorization application 1412 uses identity input from the access controller 1306 and authentication input from the questionnaire viewer 1216 to determine whether access should be granted (box 2016).

Figure 21:
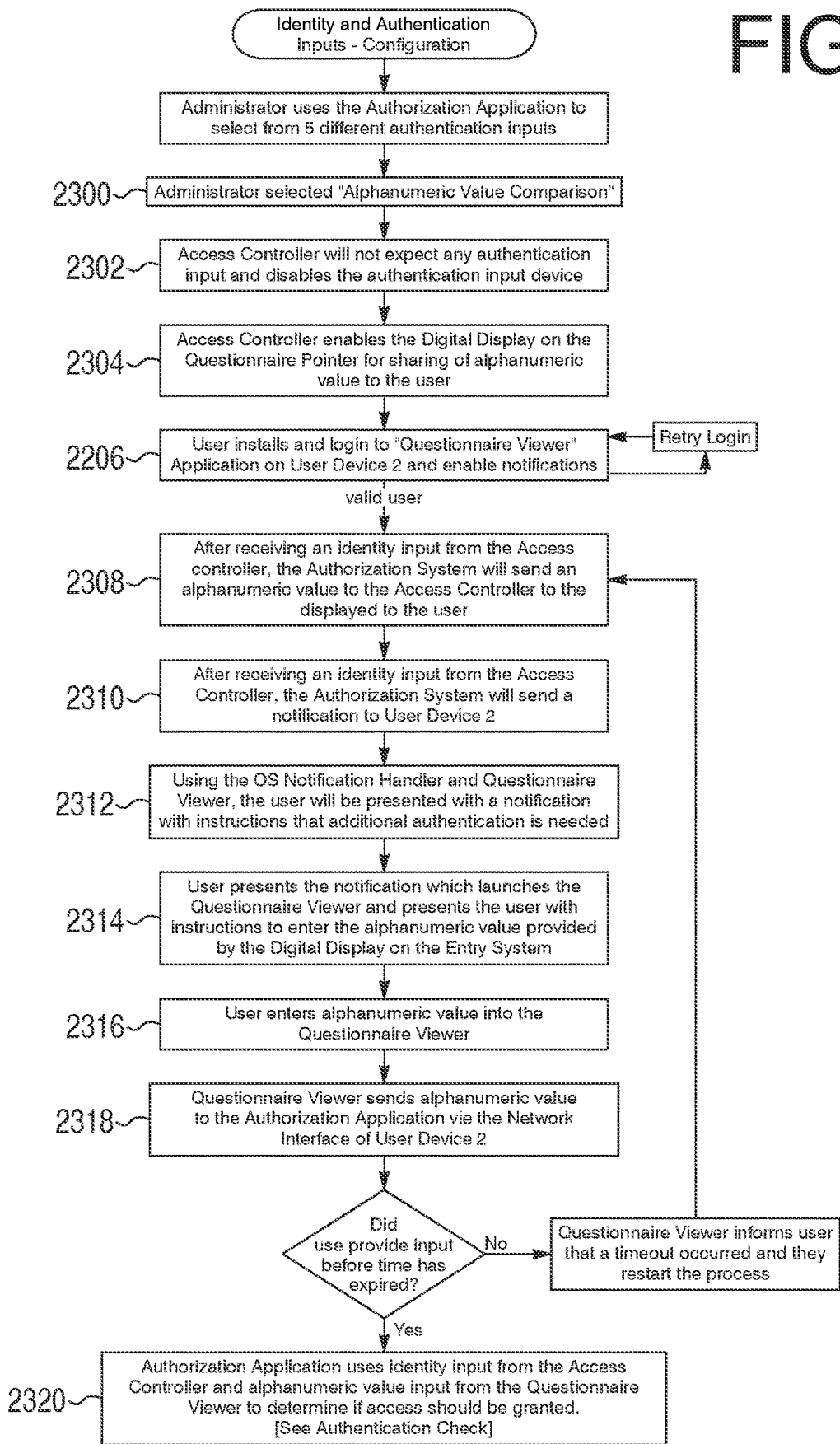
FIG. 21 is a flow chart showing the authentication input using alphanumeric value.

Referring to FIG. 21, which is a flow chart showing the authentication input using alphanumeric value (box 2300), the access controller 1306 disables the authentication input device 1312 (box 2302), and enables the digital display of the QP 1314 on the main entry system 1002 (box 2304). The user is shown an alpha numeric value on the digital display of the QP 1314 (box 2304). The user then logs into the questionnaire viewer 1216 and enables notifications on the second user device 1006b (box 2306). Preferably, the questionnaire viewer 1216 is logged on and is running in the background of the second user device 1006b. Alternatively, the user may be reminded by the RQP to log in to the questionnaire viewer 1216 on the way to the secure space 114. Once login is verified and after the authorization system 1004 receives the identity input from the access controller 1306 (box 2132 in FIG. 19), the authorization system 1004 sends an alphanumeric code to the access controller 1306 on the main entry system 1002 to be displayed to the user on the digital display of the QP 1314 for the user (box 2308), and sends a notification to the second user device 1006b (box 2310). Through the OS notification handler 1204 and the questionnaire viewer 1216 on the second user device 1006b, the user is presented with a notification and instructions that additional authentication is needed (box 2312). When the user presses the notification, the questionnaire viewer 1216 is launched to present the user with instruction to enter the alphanumeric value provided on the digital display of the QP 1314 (box 2314). The user then enters the alphanumeric value using the questionnaire viewer 1216 on the second user device 1006b (box 2316). The questionnaire viewer 1216 then sends the alphanumeric value entered by the user to the authorization application 1412 on the authorization system 1004 (box 2318) which uses the identity input from the access controller and the alpha numeric value input to determine whether access should be granted (box 2320).

Figure 22:
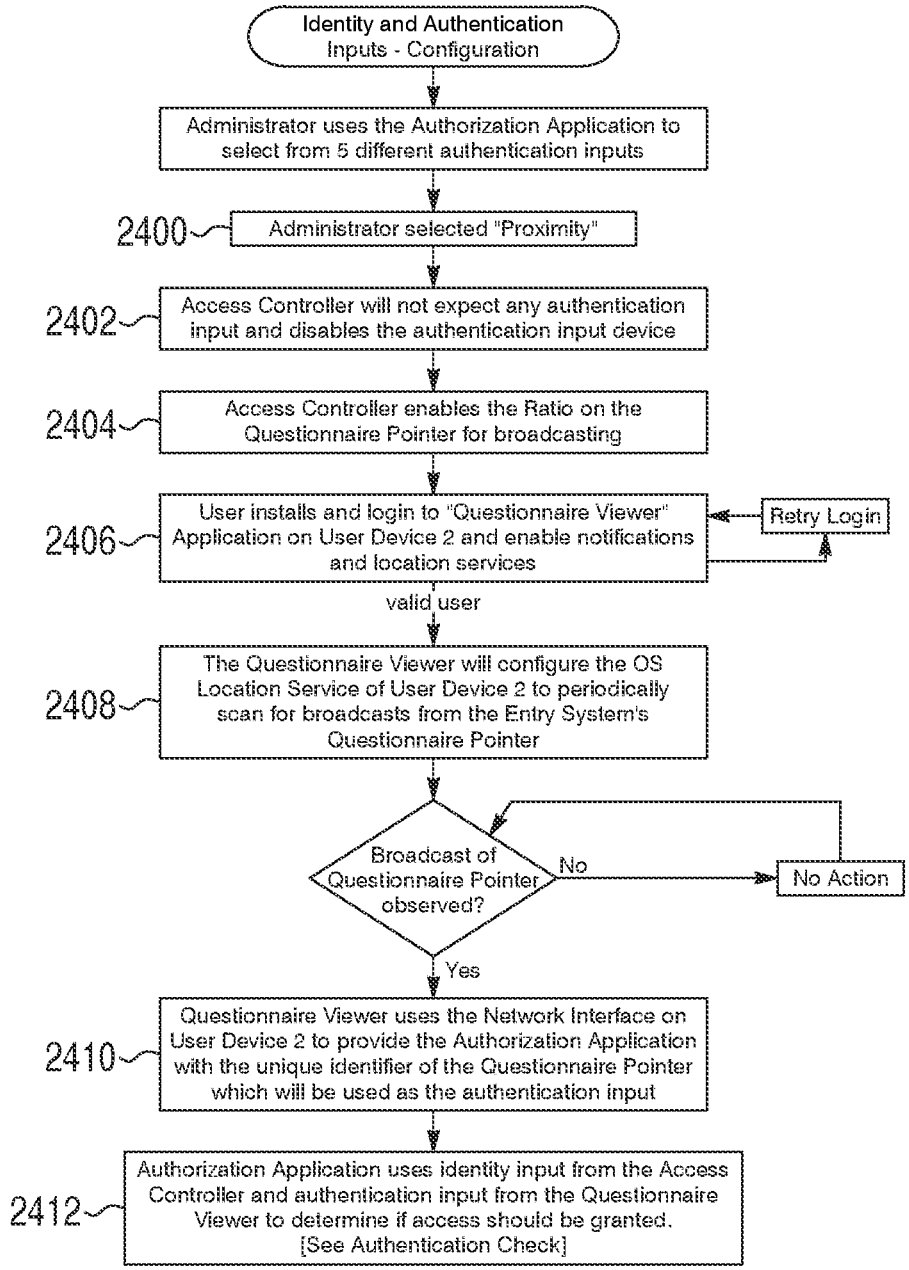
FIG. 22 is a flow chart showing the authentication input using proximity of the second user device to the main entry system.
Figure 23:
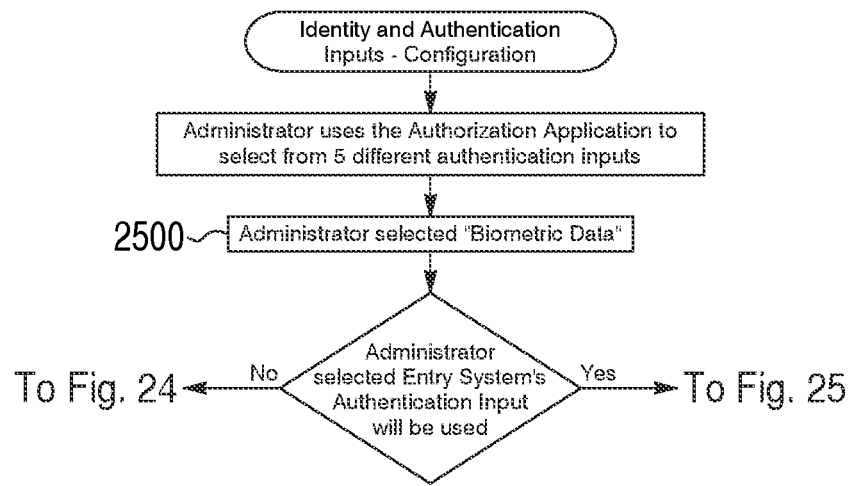
FIG. 23 is a flow chart showing the authentication input using biometric data of the user.

Referring to FIG. 22, which is a flow chart showing the authentication check using the proximity of the second user device 1006b to the main entry system 1002 (box 2300), the access controller 1306 disables the authentication input device 1312 (box 2302), and enables the radio on the QP 1314 of the main entry system 1002 for broadcasting (box 2304). The user then logs into the questionnaire viewer 1216 and enables notifications and location service on the second user device 1006b (box 2406). Preferably, the questionnaire viewer 1216 is logged on and is running in the background of the second user device 1006b. Alternatively, the user may be reminded by the RQP to log in to the questionnaire viewer 1216 on the way to the secure space 114. Once login is verified and after the authorization system 1004 receives the identity input from the access controller 1306 (box 2132 in FIG. 19), the questionnaire viewer 1216 configures the OS location service 1206 of the second user device 1006b to periodically scan for broadcasts from the QP 1314 (box 2408). Once a broadcast is detected, the questionnaire viewer 1216 uses the network interface 1200 of the second user device 1006b to provide the authorization application 1412 on the authorization system 1004 with the unique identifier broadcasted by the QP 1314 (box 2410). That unique identifier is used as the authentication input. The authorization application 1412 then uses the identity input from the access controller 1306 and the authentication input from the questionnaire viewer 1216 to determine whether access should be granted (box 2312).

Figure 24:
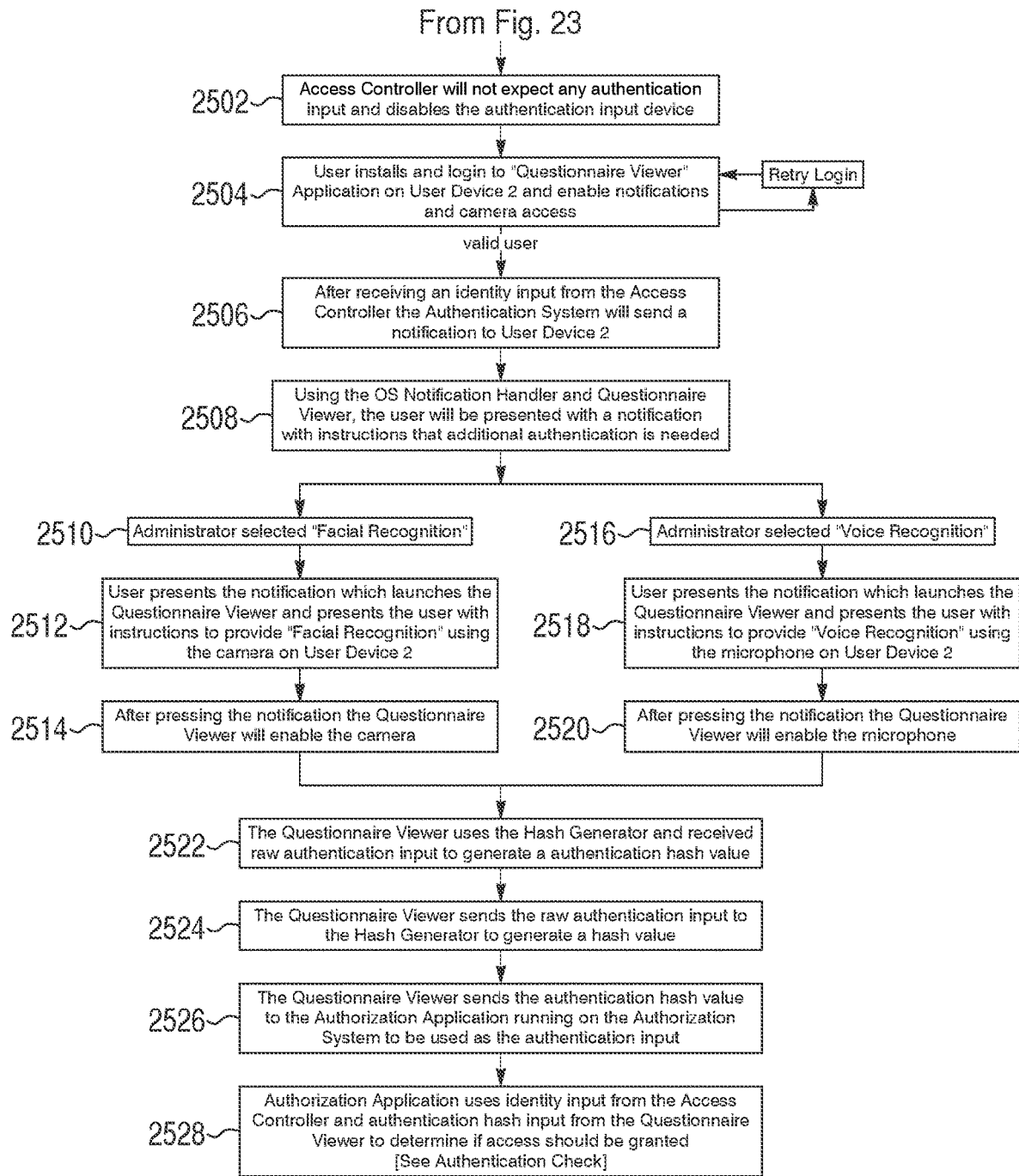
FIG. 24 is a flow chart is a flow chart showing the authentication input using biometric authentication input from the user device.

Referring to FIG. 23, which is a flow chart showing the authentication check using biometric data (box 2300), the access controller 1306 disables the authentication input device 1312 (box 2302), and enables the digital display of the QP 1314 on the main entry system 1002 (box 2304). To obtain biometric input from the user, the administrator may use the authentication input device 1312 of main entry system 1002 or the second user device 1006b. FIG. 24 is a flow chart showing the authentication check using biometric authentication input from the user device 1006b; and FIG. 25 is a flow chart showing the authentication check using biometric authentication input from the authentication input device 1312 of the main entry system 1002.

Referring to FIG. 24, if the administrator elects to use the second user device 1006b to obtain biometric data, the access controller 1306 disables the authentication input device 1312 (box 2502). The user then logs into the questionnaire viewer 1216 and enables notifications and camera and/or microphone access on the second user device 1006b (box 2504). Preferably, the questionnaire viewer 1216 is logged on and is running in the background of the second user device 1006b. Alternatively, the user may be reminded by the RQP to log in to the questionnaire viewer 1216 on the way to the secure space 114. Once login is verified and after the authorization system 1004 receives the identity input from the access controller 1306 (box 2132 in FIG. 19), the authorization system 1004 sends a notification to the second user device 1006b (box 2506). Through the OS notification handler 1204 and the questionnaire viewer 1216 on the second user device 1006b, the user is presented with a notification and instructions that additional authentication is needed (box 2508). Here, the administration can select facial recognition (box 2510) or voice recognition (box 2516) as the biometric data. If facial recognition is selected, when the user presses the notification, the questionnaire viewer 1216 is launched to present the user with instructions to provide facial recognition using the camera 1208 on the second user device 1006*b* (box 2512). The questionnaire viewer 1216 also enables the camera 1208 (box 2514) to take an image of the user's face. If voice recognition is selected by the administrator, when the user presses the notification, the questionnaire viewer 1216 is launched to present the user with instructions to provide voice recognition using the microphone 1210 on the second user device 1006*b* (box 2518). The questionnaire viewer 1216 also enables the microphone 1210 (box 2520) to record the speaking voice of the user. Once the image or voice is recorded, the questionnaire viewer 1216 uses a hash generator on the second user device 1006*b* and the raw authentication input (image or voice recording) to generate an authentication hash value of the authentication input by sending the raw authentication input to the hash generator (box 2522). The hash generator on the second user device 1006*b* uses the raw authentication input to generate the authentication has value (box 2524). The questionnaire viewer 1216 then sends the authorization hash value to the authorization application 1412 on the authorization system 1004 to be used as the authentication input (box 2526). The authorization application 1412 then uses the identity input from the access controller 1306 and the hashed authentication input from the questionnaire viewer 1216 to determine whether access should be granted (box 2528).

Figure 25:
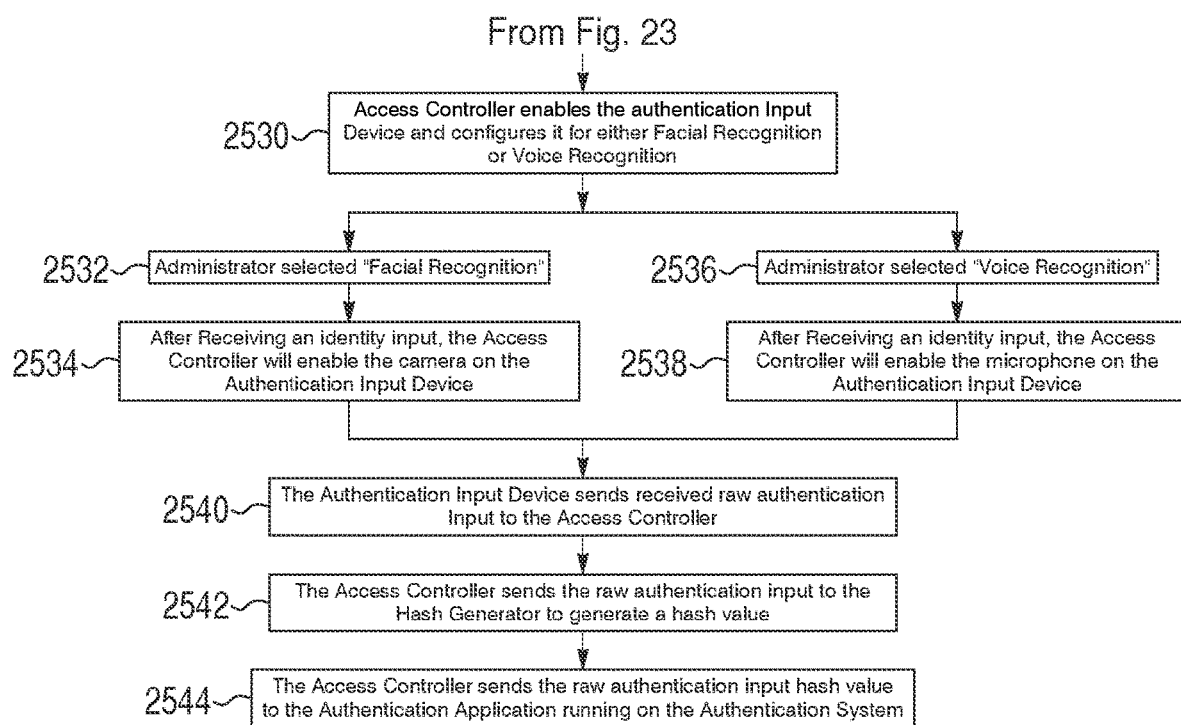
FIG. 25 is a flow chart showing the authentication input using biometric authentication input from the authentication input device 1312 of the main entry system

Referring to FIG. 25, if the administrator elects to use the authentication input device 1312 of the main entry system 1002 to obtain biometric data, the access controller 1306 enables the authentication input device 1312 (box 2530). Here, the administration can select facial recognition (box 2532) or voice recognition (box 2536) as the biometric data. If facial recognition is selected, after the authorization system 1004 receives the identity input from the access controller 1306 (box 2132 in FIG. 19), the access controller 1306 enables the camera on the authentication input device 1312 on the main entry system 1002 (box 2534) to take an image of the user's face. If voice recognition is selected, after the authorization system 1004 receives the identity input from the access controller 1306 (box 2132 in FIG. 19), the access controller 1306 enables the microphone on the authentication input device 1312 on the main entry system 1002 (box 2538) to record the talking voice of the user. Once the image or voice is recorded, the authentication input device 1312 send the raw authentication input (image or voice recording) to the access controller 1306 (box 2540) which, in turn, sends the raw authentication input to the hash generator 1308 to generate a hash value of the raw authentication input (box 2542). The access controller 1306 then sends the hash value to the authorization application 1412 on the authorization system 1004 to be used as the authentication input (box 2544). The authorization application 1412 then uses the identity input from the access controller 1306 and the hashed authentication input to determine whether access should be granted.

Figure 26:
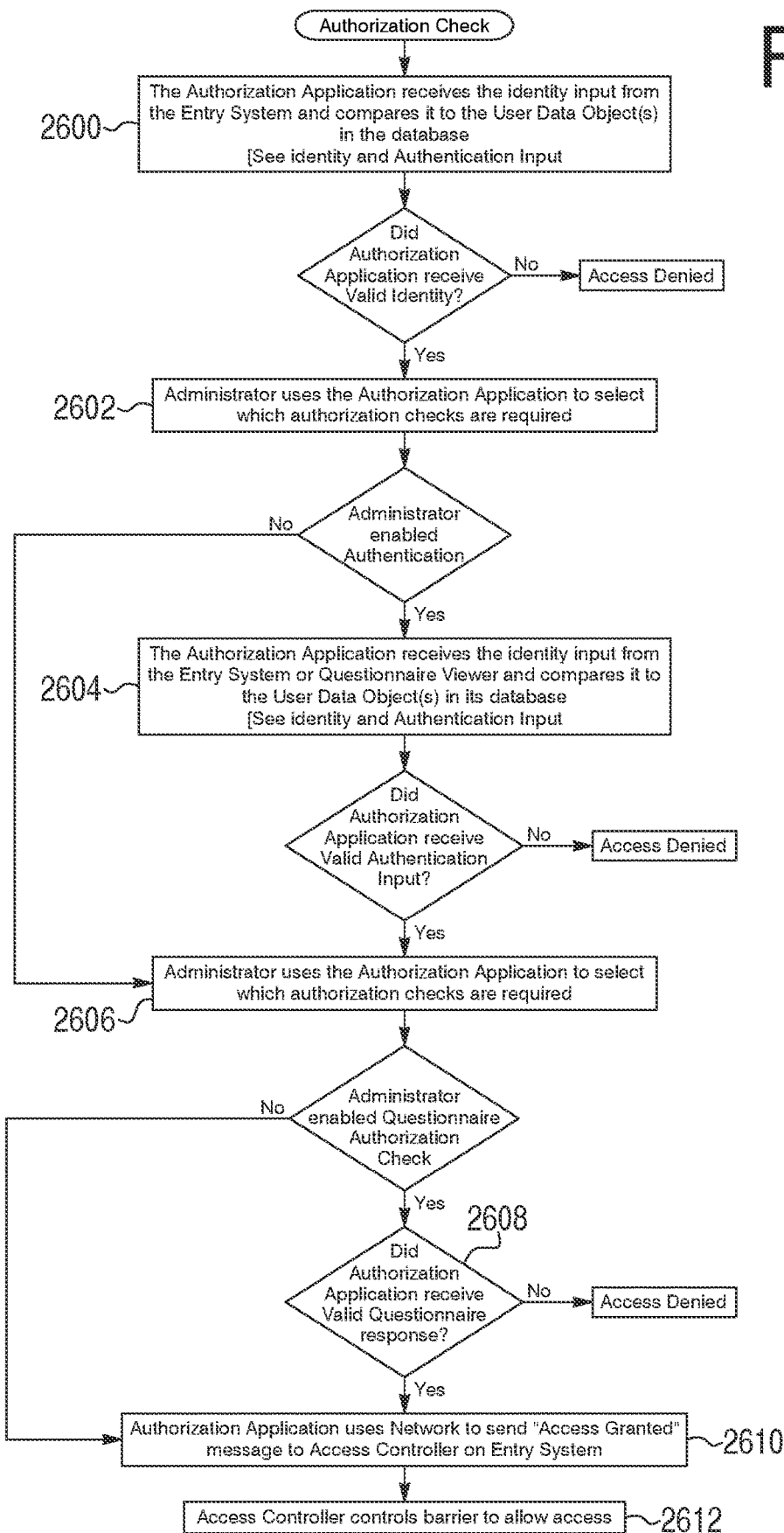
FIG. 26 is a flow chart showing the authorization check process.

FIG. 26 is a flow diagram showing the authorization check process after identity and authentication inputs have been obtained by the authorization application 1412 on the authorization system 1004. Once the identity input is received, it is checked against the user data object for the particular user in the database 1402 (box 2600). If the identity input does not match, access is denied. The administrator then uses the authorization application 1412 to select the types of authorization check required (box 2602). If authentication is enabled, the authorization application 1412 receives the authentication input from the main entry system 1002 or the questionnaire viewer 1216 of the second user device 1006*b* (see boxes 2528 of FIG. 24, 2412 of FIG. 22, 2320 of FIG. 21, and 2216 of FIG. 20) and compares it to the user data object for the particular user in the database 1402 (box 2604). If the authentication input does not match access is denied. The administrator then uses the authorization application 1412 to select the types of authorization check required (box 2606). If questionnaire authorization check is enabled, the authorization system 1004 checks whether the authorization application 1412 receives valid response(s) to the questionnaire (box 2608). If the response(s) is not valid, access is denied. If the response(s) is valid, the authorization application 1412 sends an access granted message to the access controller 1306 on the main entry system 1002 (box 2610). The access controller 1306, in turn, release the lock on the barrier to allow the user to enter the secure space 114 (box 2612).

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for entering a secure space, comprising the steps of:
providing a controlled entry system at an entrance of a building, the entry system configured to interact with a plurality of first user devices and a plurality of second user devices, the entry system comprising a main entry system controlling a barrier and an authorization system having a database and configured to validate the first and second user devices and to send a questionnaire to the second user device, wherein the second user devices, the main entry system, and the authorization system communicate with each other over a computer network;
reading one of the plurality of first users devices to obtain a unique identification;
determining from the database whether a questionnaire is required for the unique identification from information associated with the unique identification stored in the authorization system;
sending an authentication request to one of the plurality of second user devices;
receiving an authentication input in response to the authentication request from the one of the plurality of second user devices;
if a questionnaire is required, transmitting the questionnaire to the one of the plurality of second user devices;
receiving a response to the questionnaire from the one of the plurality of second user devices; comparing the unique identification, the authentication input, and the questionnaire response with information from a database; and granting access to the secure space only if the unique identification, the authentication input, and the response match the information of the database;
wherein the step of sending a questionnaire occurs when the one of the plurality of second user devices is within a predetermined distance of the entrance.

2. The method of claim 1, wherein the one of the plurality of first user devices comprises an identification card, an employee badge, a bar code, a QR code, or combinations thereof.

3. The method of claim 1, wherein the one of the plurality of second user devices comprises a smart phone, a smart watch, a laptop, or a tablet.

4. The method of claim 1, wherein the response comprises a picture of a user's face, a voice recording of the user's voice, an assigned code, or proximity of the second user device to the entrance.

5. The method of claim 1, wherein the reading step occurs at an identity input device.

6. The method of claim 5, wherein the identity input device comprises one of a RFID reader, a bar code reader, a QR reader, a cell phone, a tablet computer, or combinations thereof.

7. The method of claim 1, wherein the step of reading one of the plurality of first the user devices occurs when the one of the plurality of first users is within the predetermined distance of the entrance.

8. A controlled entrance, comprising:
a. an entryway in a building, the entryway including a barrier operable to permit access to the building through the entryway;
b. an identity input device for determining the proximity of an individual seeking access to the building through the entryway, the identity input device configured to read a first user device associated with a unique identification for the individual;
c. a questionnaire pointer operably associated with the identity input device and configured to determine whether the individual needs to submit a questionnaire;
d. an authentication input device configured to receive an authentication input from the individual;
e. an authorization system operably associated with the entryway and configured to transmit a questionnaire to a second user device associated with the individual when the second user device is within a predetermined distance of the entrance and for receiving a completed questionnaire from the second user device; and
f. an access controller operably associated with the barrier and the authorization system for operating the barrier upon determination that the unique identification, the authentication input, and the questionnaire response match the information from a database associated with the authorization system.

9. The controlled entrance of claim 8, wherein the identity input device comprises any of a RFID reader, a fingerprint scanner, a retinal scanner, a camera, a keypad, a writing pad, a voice recorder, a bar code reader, a QR reader, a cell phone, a tablet computer, or combinations of them.

10. The controlled entrance of claim 9, wherein the identity input device is configured for multi-factor authentication.

11. The controlled entrance of claim 9, wherein the identity input device is configured to identify the individual when the individual is within a defined area adjacent to the entrance.

12. The controlled entrance of claim 9, wherein a temperature sensor and/or camera is operably associated with the entryway for determining at least one of the body temperature and facial expression of the individual.

13. The controlled entrance of claim 9, wherein a wired or wireless interface interconnects the identity input device with the control system and with the authorization system.

14. The controlled entrance of claim 13, wherein the wireless interface operate via at leas one of cellular (3G/4G/5G), Bluetooth, Bluetooth Lower Energy, WiFi, TCP/IP, near field communication (NFC).

15. The controlled entrance of claim 8, wherein the authentication input device comprises any of a camera, a microphone, or combinations of any of them.

16. The controlled entrance of claim 8, wherein the questionnaire comprises a non-disclosure agreement (NDA), a security clearance, a safety protocol, a code of conduct, a non-compete agreement, an engagement census, a health questionnaire, or combinations of them.

17. The controlled entrance of claim 8, wherein:
a. the barrier is a door pivotally mounted to a doorframe;
b. the barrier includes a motor operable in response to an actuation signal from the authorization system for pivoting the door between an open position and a closed position; and
c. the identity input device is mounted proximate the doorframe.

18. The entryway of claim 8, wherein a database contains individual identification information, questionnaire information, and authentication information.

* * * * *